(12) United States Patent
Wang et al.

(10) Patent No.: US 11,793,071 B2
(45) Date of Patent: Oct. 17, 2023

(54) ORGANIC COMPOUND, ELECTROLUMINESCENT MATERIAL, AND USE THEREOF

(71) Applicant: Wuhan Tianma Micro-Electronics Co., Ltd., Wuhan (CN)

(72) Inventors: Kui Wang, Wuhan (CN); You Gao, Shanghai (CN)

(73) Assignee: Wuhan Tianma Micro-Electronics Co., Ltd., Wuhan (CN)

( * ) Notice: Subject to any disclaimer, the term of this patent is extended or adjusted under 35 U.S.C. 154(b) by 530 days.

(21) Appl. No.: 17/126,785

(22) Filed: Dec. 18, 2020

(65) Prior Publication Data

US 2021/0104678 A1    Apr. 8, 2021

(30) Foreign Application Priority Data

Sep. 22, 2020 (CN) .......................... 202011003246.6

(51) Int. Cl.
| | | |
|---|---|---|
| H10K 85/60 | (2023.01) | |
| C07D 487/22 | (2006.01) | |
| C09K 11/06 | (2006.01) | |
| H10K 50/11 | (2023.01) | |
| H10K 101/10 | (2023.01) | |

(52) U.S. Cl.
CPC ......... *H10K 85/654* (2023.02); *C07D 487/22* (2013.01); *C09K 11/06* (2013.01); *H10K 85/6572* (2023.02); *C09K 2211/1018* (2013.01); *H10K 50/11* (2023.02); *H10K 2101/10* (2023.02)

(58) Field of Classification Search
CPC .. H01K 85/854; H01K 85/6572; H01K 50/11; H01K 2101/10; C07D 487/22; C09K 11/06; C09K 2211/1018

USPC ........................................................ 428/690
See application file for complete search history.

(56) References Cited

U.S. PATENT DOCUMENTS

| | | | |
|---|---|---|---|
| 2018/0015180 A1* | 1/2018 | Castaigne | A61P 15/00 |
| 2018/0026210 A1* | 1/2018 | Dyatkin | H10K 85/40 257/40 |
| 2018/0182981 A1* | 6/2018 | Chen | C09K 11/025 |
| 2018/0337350 A1* | 11/2018 | Li | C07F 15/006 |
| 2019/0036042 A1* | 1/2019 | Kim | H10K 85/346 |
| 2019/0058130 A1* | 2/2019 | Aguilera-Iparraguirre | H10K 85/6572 |
| 2019/0074455 A1* | 3/2019 | Chen | C07F 15/0086 |

(Continued)

*Primary Examiner* — Michael M. Bernshteyn
(74) *Attorney, Agent, or Firm* — von Briesen & Roper, s.c.

(57) ABSTRACT

Provided are an organic compound, an electroluminescent material, and a use thereof. The organic compound has a structure represented by Formula I and is a carbazole olefin-like compound which is beneficial for improving the amorphous performance, thermal stability, and glass transition temperature of the material. The organic compound has appropriate HOMO energy level and LUMO energy level and a relatively high triplet energy level and can inhabit the transfer of triplet energy from a guest back to a host and reduce a driving voltage of a device. The organic compound, as a host material, has a relatively high carrier transport rate and balanced carrier transport performance, so as to facilitate the balance of hole and electron currents in the device, obtain a wider carrier recombination region, significantly improve light emitting efficiency and external quantum efficiency of the device, and reduce a turn-on voltage and power consumption of the device.

15 Claims, 1 Drawing Sheet

(56) References Cited

U.S. PATENT DOCUMENTS

2019/0214584 A1* 7/2019 Chen .................. H10K 85/6572
2019/0319196 A1* 10/2019 Sim ...................... C07D 403/10

* cited by examiner

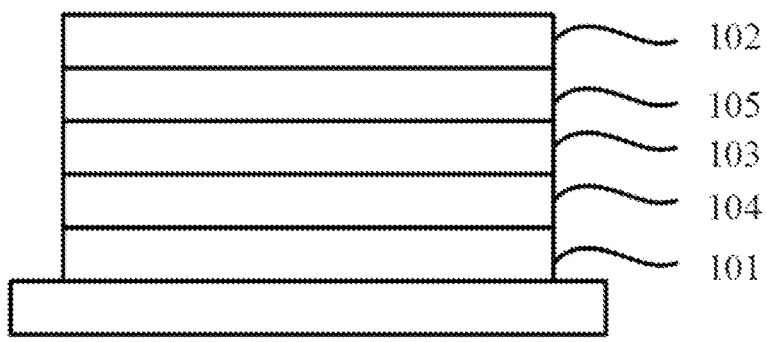

ORGANIC COMPOUND, ELECTROLUMINESCENT MATERIAL, AND USE THEREOF

CROSS-REFERENCE TO RELATED APPLICATION(S)

This application claims priority to Chinese Patent Application No. 202011003246.6 filed Sep. 22, 2020, the disclosure of which is incorporated herein by reference in its entirety.

TECHNICAL FIELD

The present disclosure belongs to the field of organic electroluminescent materials and, in particular, relates to an organic compound, an electroluminescent material, and a use thereof.

BACKGROUND

Organic electroluminescence (EL) is an emerging technology that has become increasingly mature and has a huge application prospect in the field of optoelectronic devices. Since 1987 when organic electroluminescent materials and devices such as an organic light emitting diodes (OLED) emerged, the OLED has attracted wide attention in the scientific community and the industry and been actively developed. The OLED is regarded as the most competitive technology in the new generation of display technologies. The OLED technology has many characteristics such as low power consumption, a quick response speed, ease to bend, a wide viewing angle, large area display, and full light emitting colors, and is compatible with various existing standards and technologies so as to make low-cost light emitting devices. The OLED technology has been widely applied in the fields of flat panel display, flexible display, solid-state lighting and in-vehicle display.

In OLED devices, the choice of materials is crucial since structures and properties of the materials directly affect final performance of the devices. Light emitting materials in the OLED devices are roughly divided into electroluminescence and electrophosphorescence according to a light emitting mechanism. The electroluminescence is radiative decay and transition of singlet excitons, while the electrophosphorescence is light emitting due to the radiative decay of triplet excitons to a ground state. According to the theory of quantum spin-statistics, singlet excitons and triplet excitons are formed at a ratio of 1:3. Therefore, the internal quantum efficiency of electroluminescent materials does not exceed 25%, and the external quantum efficiency of the electroluminescent materials is generally less than 5%; while the internal quantum efficiency of electrophosphorescent materials reaches 100% in theory, and the external quantum efficiency of the electrophosphorescent materials can reach 20%. In 1998, Professors Baldo and Forrest etc. found that triplet phosphorescence can be utilized at room temperature to increase the original upper limit of internal quantum efficiency to 100%. The formed complex mixes energy levels of a singlet excited state and a triplet excited state by use of a heavy atom effect and strong spin-orbit coupling, so that the originally forbidden triplet energy emits light in the form of phosphorescence, and quantum efficiency is thus greatly improved. A phosphorescent material and an electroluminescent device including the same have been prepared for the first time.

With the continuous development of the OLED technology, almost all light emitting layers in organic OLEDs use a host-guest light emitting system structure, that is, a guest light emitting material is doped in a host light emitting body, and energy is transferred from the host to the guest, so that a dopant is excited to emit light. At present, doped materials have reached a relatively mature level of commercialization, while host materials still have a relatively large research space.

CN103804246A has disclosed an electron input type red phosphorescent compound, a preparation method thereof, and an organic electroluminescent device. The electron input type red phosphorescent compound contains a fluorenyl group and a benzenesulfonyl group, has an electron transport capability, and is beneficial to a carrier transport balance. CN103012481A has disclosed a phosphorescent host material and a preparation method and an application thereof. The phosphorescent host material is composed of carbazole with a hole transport capability and a unit of diphenylphosphine oxide and benzothiazole/benzoxazole with an electron transport capability, has good thermal stability and hole transport and electron transport properties, and can be used as red and green phosphorescent host materials. CN103804332A has disclosed an electron transport type red phosphorescent compound and a preparation method and an application thereof. The phosphorescent compound contains a dibenzofuryl group and a benzenesulfonyl group, has a relatively high triplet energy level, can avoid the transfer of energy back to a host material, and is beneficial to a carrier transport balance.

In the current research status of organic electrophosphorescent materials, green electrophosphorescent devices and red electrophosphorescent devices have reached the level of commercial applications in terms of efficiency, color purity, and stability, but there are few types of blue electrophosphorescent devices which have the disadvantages of a short lifetime, poor device stability, a lack of pure blue materials and insufficient device efficiency, which greatly restricts the further development of full-color OLED display devices.

Therefore, it is a research focus in the art to develop organic electroluminescent materials, especially blue phosphorescent materials with better performance to meet the usage requirements of high-performance blue phosphorescent OLEDs.

SUMMARY

To develop more types of organic electroluminescent materials with better performance, a first object of the present disclosure is to provide an organic compound having a structure represented by Formula I:

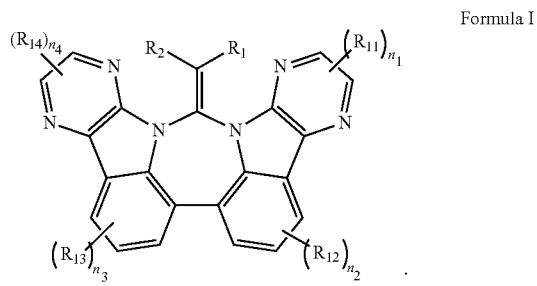

Formula I

In Formula I, $R_1$ and $R_2$ are each independently selected from any one of substituted or unsubstituted C6 to C30 aryl and substituted or unsubstituted C2 to C30 heteroaryl.

In Formula I, $R_{11}$, $R_{12}$, $R_{13}$, and $R_{14}$ are each independently selected from any one of halogen, cyano, substituted or unsubstituted C1 to C20 straight or branched chain alkyl, C1 to C20 alkoxy, C1 to C20 alkylthio, substituted or unsubstituted C3 to C20 cycloalkyl, substituted or unsubstituted C6 to C30 aryl, and substituted or unsubstituted C2 to C30 heteroaryl.

In Formula I, $n_1$ and $n_4$ are each independently selected from an integer between 0 and 2, for example, 0, 1, or 2.

In Formula I, $n_2$ and $n_3$ are each independently selected from an integer between 0 and 3, for example, 0, 1, 2, or 3.

In the present disclosure, C6 to C30 may each independently be C6, C8, C10, C12, C13, C14, C15, C16, C18, C20, C22, C24, C26, or C28, etc.

C2 to C30 may each independently be C2, C3, C4, C5, C6, C8, C10, C12, C13, C14, C15, C16, C18, C20, C22, C24, C26, or C28, etc.

C1 to C20 may each independently be C2, C3, C4, C5, C6, C8, C10, C12, C14, C16, C18, or C19, etc.

C3 to C20 may each independently be C4, C5, C6, C8, C10, C12, C13, C14, C15, C16, C18, or C19, etc.

In the present disclosure, halogen includes fluorine, chlorine, bromine, or iodine.

The organic compound provided by the present disclosure has a relatively high triplet energy level through the coordination of a parent core structure and a substituent in a molecular structure and can inhibit the transfer of triplet energy from a guest back to a host, thereby confining triplet excitons in a light emitting layer; meanwhile, the organic compound has a HOMO energy level and a LUMO energy level which match an energy level of an adjacent carrier transport layer to reduce hole and electron injection barriers and reduce a driving voltage of the device; in addition, the widths of the HOMO energy level and the LUMO energy level of the organic compound are larger than those of a phosphorescent guest material, which is beneficial to the energy transfer from the host to the guest and the direct trapping of carriers on a phosphorescent guest. Moreover, the organic compound, as a host material, has a relatively high carrier transport rate and balanced carrier transport performance, so as to facilitate the balance of hole and electron currents in the device and obtain a wider carrier recombination region; and the organic compound further has good thermal stability and film formability, so as to facilitate the formation of a stable and uniform thin film in a vacuum thermal evaporation process, reduce phase separation, and maintain device stability.

A second object of the present disclosure is to provide an electroluminescent material including the organic compound as described for the first object.

A third object of the present disclosure is to provide a display panel. The display panel includes an OLED device, the OLED device includes an anode, a cathode and an organic thin film layer disposed between the anode and the cathode, and a material of the organic thin film layer includes the electroluminescent material as described for the second object.

A fourth object of the present disclosure is to provide an electronic apparatus including the display panel as described for the third object.

Compared with the related art, the present disclosure has beneficial effects described below.

The organic compound provided by the present disclosure has a carbazole olefin-like structure which endows an intramolecular group with a non-planar configuration and is beneficial for improving amorphous performance, thermal stability, and glass transition temperature of the material. The organic compound has appropriate HOMO energy level and LUMO energy level and a relatively high triplet energy level $T_1$ which is above 2.89 eV or even higher than 3.0 eV, and can inhabit the transfer of triplet energy from the guest back to the host, so as to confine triplet excitons in the light emitting layer and reduce the driving voltage of the device. The organic compound, as the host material, has a relatively high carrier transport rate and balanced carrier transport performance, so as to facilitate the balance of hole and electron currents in the device and obtain a wider carrier recombination region. The organic compound is especially appropriate for being applied in the light emitting layer of the OLED device as a phosphorescent host material and can significantly improve the light emitting efficiency and the external quantum efficiency of the device, reduce efficiency roll-off under high brightness, reduce a turn-on voltage and energy consumption of the device, and prolong a service life of the device.

BRIEF DESCRIPTION OF DRAWINGS

FIG. 1 is a structural diagram of an OLED device provided by the present disclosure, where 101 denotes an anode, 102 denotes a cathode, 103 denotes a light emitting layer, 104 denotes a first organic thin film layer, and 105 denotes a second organic thin film layer.

DETAILED DESCRIPTION

The solutions of the present disclosure are further described below through specific examples. Those skilled in the art should understand that the examples described herein are used for a better understanding of the present disclosure and should not be construed as specific limitations to the present disclosure.

A first object of the present disclosure is to provide an organic compound, where the organic compound has a structure represented by Formula I:

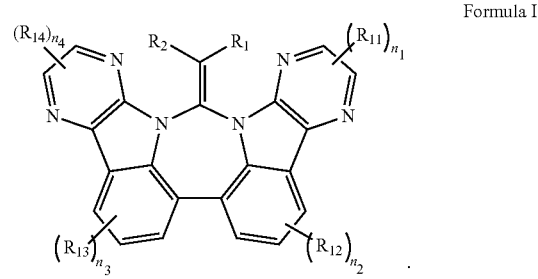

Formula I

In Formula I, $R_1$ and $R_2$ are each independently selected from any one of substituted or unsubstituted C6 to C30 aryl and substituted or unsubstituted C2 to C30 heteroaryl.

In Formula I, $R_{11}$, $R_{12}$, $R_{13}$, and $R_{14}$ are each independently selected from any one of halogen, cyano, substituted or unsubstituted C1 to C20 straight or branched chain alkyl, C1 to C20 alkoxy, C1 to C20 alkylthio, substituted or unsubstituted C3 to C20 cycloalkyl, substituted or unsubstituted C6 to C30 aryl, and substituted or unsubstituted C2 to C30 heteroaryl.

In Formula I, $n_1$ and $n_4$ are each independently selected from an integer between 0 and 2, for example, 0, 1, or 2.

In Formula I, $n_2$ and $n_3$ are each independently selected from an integer between 0 and 3, for example, 0, 1, 2, or 3.

In the present disclosure, C6 to C30 may each independently be C6, C8, C10, C12, C13, C14, C15, C16, C18, C20, C22, C24, C26, or C28, etc.

C2 to C30 may each independently be C2, C3, C4, C5, C6, C8, C10, C12, C13, C14, C15, C16, C18, C20, C22, C24, C26, or C28, etc.

C1 to C20 may each independently be C2, C3, C4, C5, C6, C8, C10, C12, C14, C16, C18, or C19, etc.

C3 to C20 may each independently be C4, C5, C6, C8, C10, C12, C13, C14, C15, C16, C18, or C19, etc.

In the present disclosure, halogen includes fluorine, chlorine, bromine, or iodine. The same expression hereinafter has the same meaning.

The organic compound provided by the present disclosure has a carbazole olefin-like structure which endows an intramolecular group of the organic compound with a non-planar configuration and is beneficial for improving the amorphous performance, thermal stability, and glass transition temperature of the material, where $T_g$ reaches 112 to 126° C.; and the organic compound has good thermal stability and film formability, so as to facilitate the formation of a stable and uniform thin film in a vacuum thermal evaporation process, reduce phase separation, and maintain device stability. Through a special design of a molecular structure, the organic compound has a relatively high triplet energy level $T_1$ which reaches 2.89 to 3.03 eV, thereby inhibiting the transfer of triplet energy from a guest back to a host and confining triplet excitons in a light emitting layer; meanwhile, the organic compound has an appropriate HOMO energy level and LUMO energy level which can match an energy level of an adjacent carrier transport layer, to reduce hole and electron injection barriers and reduce a driving voltage of the device.

The organic compound provided by the present disclosure is appropriate for use as a phosphorescent host material of an OLED device, and has a triplet energy level higher than that of a blue guest (a triplet energy level of a blue FIrpic guest is 2.65 eV, and triplet energy levels of deep blue FCNIrpic and FIr6 guests are 2.74 eV and 2.73 eV respectively), so the organic compound is especially appropriate for being applied in blue phosphorescent OLEDs.

In an embodiment, substituents in substituted aryl, substituted heteroaryl, substituted straight or branched chain alkyl, and substituted cycloalkyl are each independently selected from at least one of halogen, cyano, halogenated or unsubstituted C1 to C10 (for example, C2, C3, C4, C5, C6, C7, C8, or C9) straight or branched chain alkyl, C6 to C18 (for example, C6, C9, C10, C12, C14, C16, or C18, etc.) aryl, C2 to C18 (for example, C3, C4, C5, C6, C8, C10, C12, C14, C16, or C18, etc.) heteroaryl, C6 to C18 (for example, C6, C9, C10, C12, C14, C16, or C18, etc.) arylamino, C1 to C10 (for example, C2, C3, C4, C5, C6, C7, C8, or C9) alkoxy, and C1 to C10 (for example, C2, C3, C4, C5, C6, C7, C8, or C9) alkylthio.

In an embodiment, $R_1$ and $R_2$ are each independently selected from any one of the following groups or any one of the following groups substituted with a substituent:

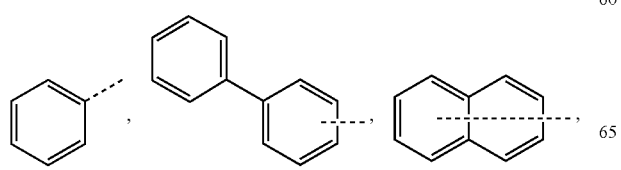

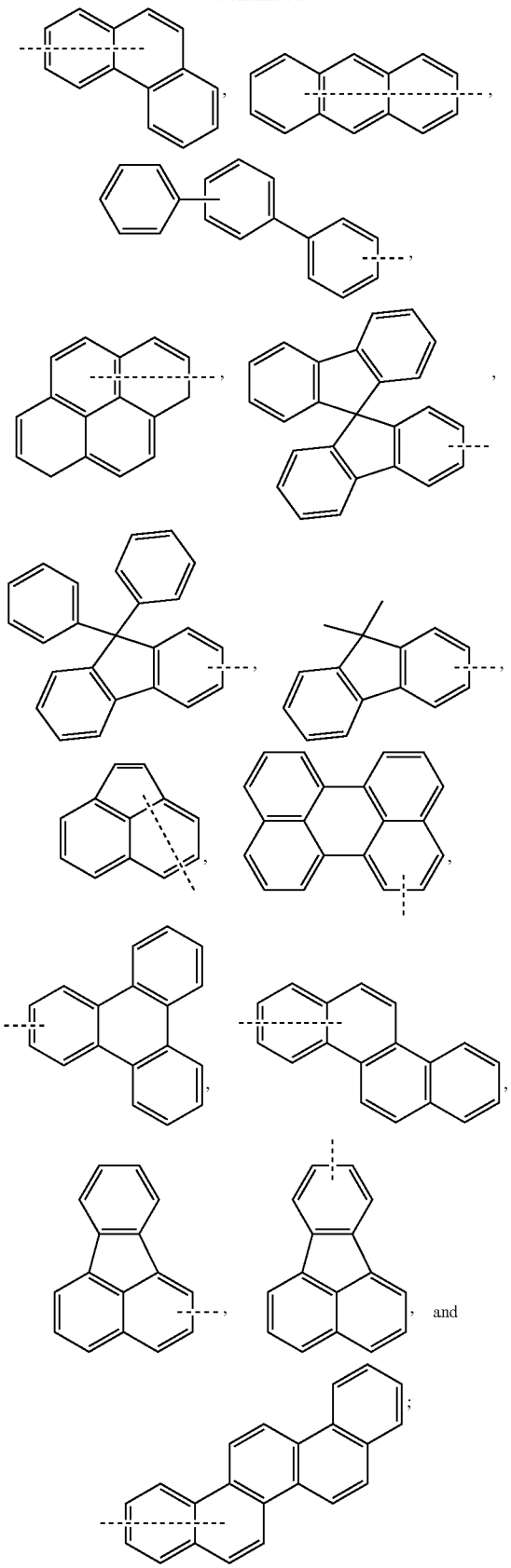

where the dashed line represents a linkage site of the group.

In an embodiment, the substituent is selected from at least one of halogen, cyano, halogenated or unsubstituted C1 to C10 (for example, C2, C3, C4, C5, C6, C7, C8, or C9) straight or branched chain alkyl, C6 to C18 (for example, C6, C9, C10, C12, C14, C16, or C18, etc.) aryl, C2 to C18 (for example, C3, C4, C5, C6, C8, C10, C12, C14, C16, or C18, etc.) heteroaryl, C1 to C10 (for example, C2, C3, C4, C5, C6, C7, C8, or C9) alkoxy, and C1 to C10 (for example, C2, C3, C4, C5, C6, C7, C8, or C9) alkylthio.

In an embodiment, $R_1$ and $R_2$ are each independently selected from any one of the following groups:

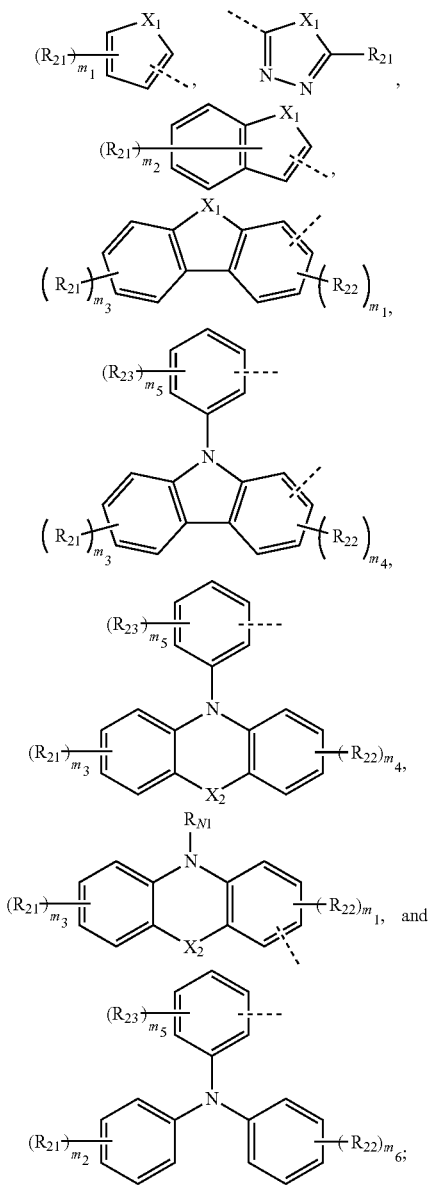

where the dashed line represents a linkage site of the group.

$X_1$ is selected from O, S, or N—$R_{N2}$.

$X_2$ is selected from O, S, N—$R_{N3}$, or $CR_{C1}R_{C2}$.

$R_{N1}$, $R_{N2}$, $R_{N3}$, $R_{C1}$, and $R_{C2}$ are each independently selected from hydrogen, unsubstituted or RA-substituted C1 to C10 (for example, C2, C3, C4, C5, C6, C7, C8, or C9) straight or branched chain alkyl, unsubstituted or $R_{x1}$-substituted C6 to C18 (for example, C6, C9, C10, C12, C14, C16, or C18, etc.) aryl, and unsubstituted or $R_{x1}$-substituted C2 to C18 (for example, C3, C4, C5, C6, C8, C10, C12, C14, C16, or C18, etc.) heteroaryl.

$R_{21}$, $R_{22}$, $R_{23}$, and $R_{x1}$ are each independently selected from any one of halogen, cyano, halogenated or unsubstituted C1 to C10 (for example, C2, C3, C4, C5, C6, C7, C8, or C9) straight or branched chain alkyl, C6 to C18 (for example, C6, C9, C10, C12, C14, C16, or C18, etc.) aryl, C2 to C18 (for example, C3, C4, C5, C6, C8, C10, C12, C14, C16, or C18, etc.) heteroaryl, C6 to C18 (for example, C6, C9, C10, C12, C14, C16, or C18, etc.) arylamino, C1 to C10 (for example, C2, C3, C4, C5, C6, C7, C8, or C9) alkoxy, and C1 to C10 (for example, C2, C3, C4, C5, C6, C7, C8, or C9) alkylthio.

$m_1$ is selected from an integer between 0 and 3, for example, 0, 1, 2, or 3.

$m_2$ and $m_6$ are each independently selected from an integer between 0 and 5, for example, 0, 1, 2, 3, 4, or 5.

$m_3$, $m_4$, and $m_5$ are each independently selected from an integer between 0 and 4, for example, 0, 1, 2, 3, or 4.

In an embodiment, $R_1$ and $R_2$ are each independently selected from any one of the following groups or any one of the following groups substituted with a substituent:

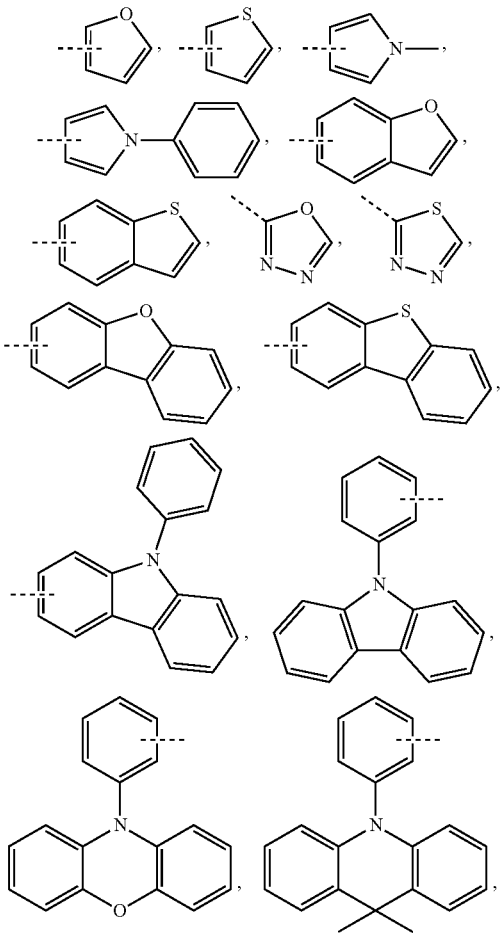

-continued

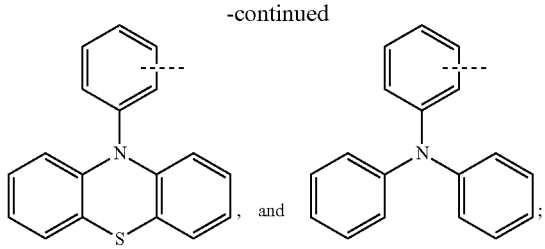

where the dashed line represents a linkage site of the group.

The substituent is selected from at least one of halogen, cyano, halogenated or unsubstituted C1 to C10 (for example, C2, C3, C4, C5, C6, C7, C8, or C9) straight or branched chain alkyl, C6 to C18 (for example, C6, C9, C10, C12, C14, C16, or C18, etc.) aryl, C2 to C18 (for example, C3, C4, C5, C6, C8, C10, C12, C14, C16, or C18, etc.) heteroaryl, C1 to C10 (for example, C2, C3, C4, C5, C6, C7, C8, or C9) alkoxy, and C1 to C10 (for example, C2, C3, C4, C5, C6, C7, C8, or C9) alkylthio.

In an embodiment, $R_1$ and $R_2$ are each independently selected from any one of the following groups:

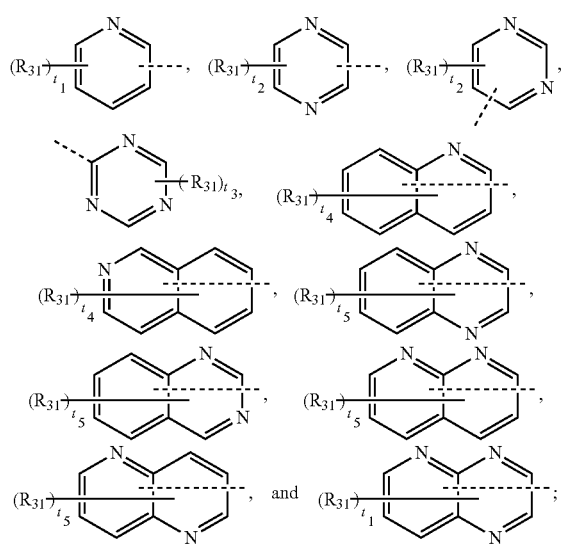

where the dashed line represents a linkage site of the group.

$R_{31}$ is each independently selected from any one of halogen, cyano, halogenated or unsubstituted C1 to C10 (for example, C2, C3, C4, C5, C6, C7, C8, or C9) straight or branched chain alkyl, C6 to C18 (for example, C6, C9, C10, C12, C14, C16, or C18, etc.) aryl, C2 to C18 (for example, C3, C4, C5, C6, C8, C10, C12, C14, C16, or C18, etc.) heteroaryl, C1 to C10 (for example, C2, C3, C4, C5, C6, C7, C8, or C9) alkoxy, and C1 to C10 (for example, C2, C3, C4, C5, C6, C7, C8, or C9) alkylthio.

$t_1$ is selected from an integer between 0 and 4, for example, 0, 1, 2, 3, or 4.

$t_2$ is selected from an integer between 0 and 3, for example, 0, 1, 2, or 3.

$t_3$ is selected from an integer between 0 and 2, for example, 0, 1, or 2.

$t_4$ is selected from an integer between 0 and 6, for example, 0, 1, 2, 3, 4, 5, or 6.

$t_5$ is selected from an integer between 0 and 5, for example, 0, 1, 2, 3, 4, or 5.

In an embodiment, $R_1$ and $R_2$ are each independently selected from any one of the following groups or any one of the following groups substituted with a substituent:

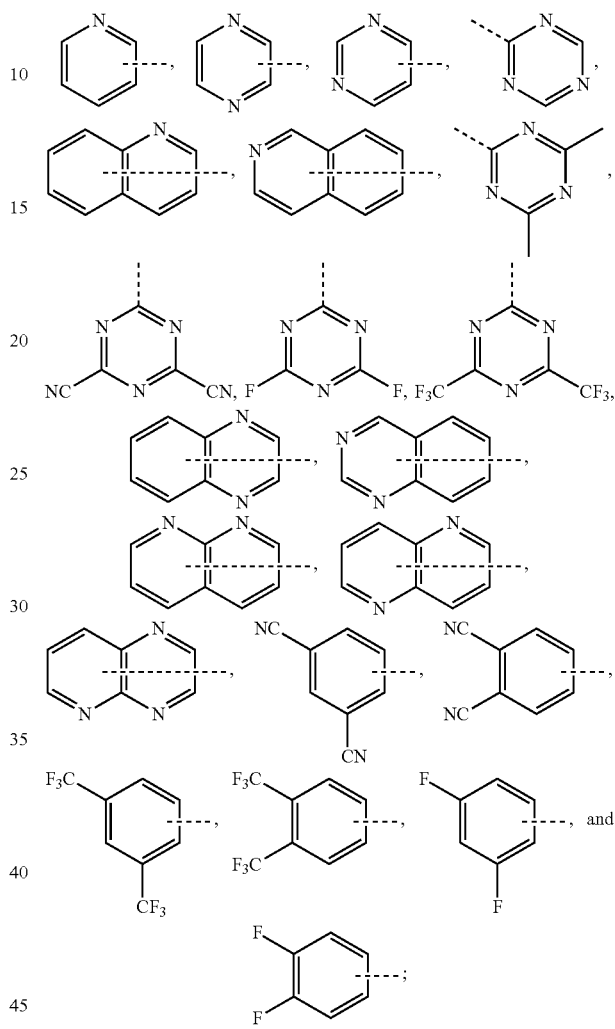

where the dashed line represents a linkage site of the group.

The substituent is selected from at least one of halogen, cyano, halogenated or unsubstituted C1 to C10 (for example, C2, C3, C4, C5, C6, C7, C8, or C9) straight or branched chain alkyl, C6 to C18 (for example, C6, C9, C10, C12, C14, C16, or C18, etc.) aryl, C2 to C18 (for example, C3, C4, C5, C6, C8, C10, C12, C14, C16, or C18, etc.) heteroaryl, C1 to C10 (for example, C2, C3, C4, C5, C6, C7, C8, or C9) alkoxy, and C1 to C10 (for example, C2, C3, C4, C5, C6, C7, C8, or C9) alkylthio.

In an embodiment, $R_1$ and $R_2$ are the same substituent.

In an embodiment, at least one of $R_1$ or $R_2$ is an electron withdrawing group.

In the present disclosure, the "electron withdrawing group" refers to a group capable of reducing an electron cloud density on a benzene ring and illustratively includes, but is not limited to, cyano, cyano-substituted aryl or heteroaryl, nitrogen-containing heteroaryl (such as pyridyl, pyrazinyl, pyrimidinyl, pyridazinyl, triazinyl, quinolyl, isoquinolyl, benzopyrazinyl, benzopyridazinyl, benzopyrimidinyl, pyridopyridyl, or pyridopyrazinyl), a fluorine-containing substituent (such as fluorine, trifluoromethyl, or perfluoroethyl), and aryl or heteroaryl substituted with the fluorine-containing substituent, etc.

In an embodiment, $R_{11}$, $R_{12}$, $R_{13}$, and $R_{14}$ are each independently selected from halogen, cyano, substituted or unsubstituted C1 to C5 (for example, C1, C2, C3, C4, or C5) straight or branched chain alkyl, substituted or unsubstituted C6 to C12 (for example, C6, C9, C10, or C12, etc.) aryl, or substituted or unsubstituted C2 to C12 (for example, C3, C4, C5, C6, C9, C10, or C12, etc.) heteroaryl; and the substituent is selected from at least one of halogen, cyano, and halogenated or unsubstituted C1 to C5 (for example, C1, C2, C3, C4, or C5) straight or branched chain alkyl.

In an embodiment, $R_{11}$, $R_{12}$, $R_{13}$, and $R_{14}$ are each independently selected from any one of halogen, cyano, C1 to C3 straight or branched chain alkyl (for example, methyl, ethyl, n-propyl, or isopropyl), unsubstituted or R'-substituted phenyl, unsubstituted or R'-substituted biphenyl, unsubstituted or R'-substituted naphthyl, unsubstituted or R'-substituted pyridyl, unsubstituted or R'-substituted pyrazinyl, unsubstituted or R'-substituted triazinyl, unsubstituted or R'-substituted quinolyl, unsubstituted or R'-substituted isoquinolyl, unsubstituted or R'-substituted benzoxazolyl, and unsubstituted or R'-substituted pyrimidinyl; where R' is selected from halogen or cyano.

In an embodiment, the organic compound is selected from any one of the following compounds M1 to M80:

M1

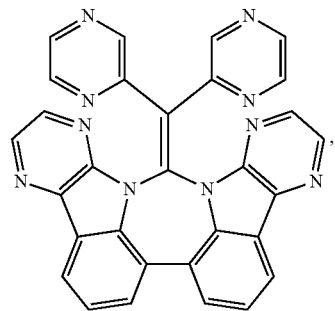

M2

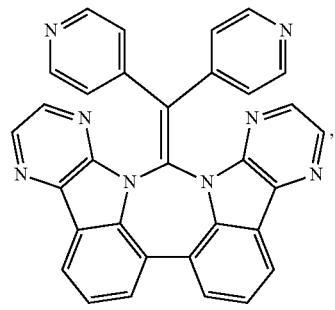

M3

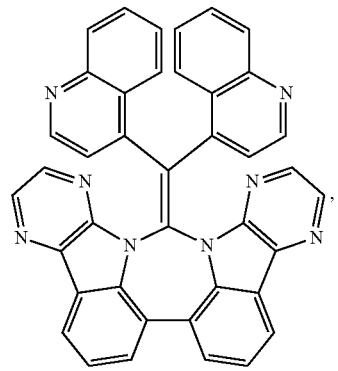

M4

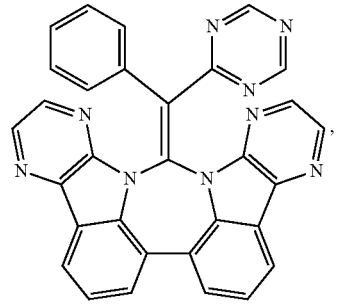

M5

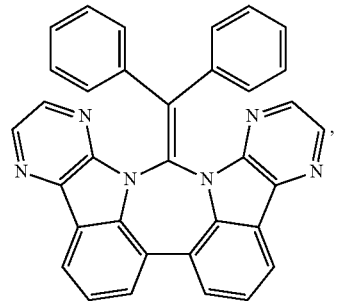

M6

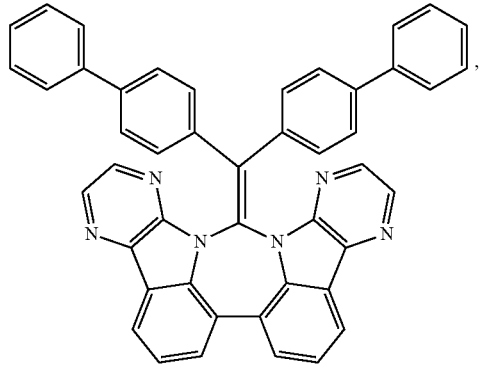

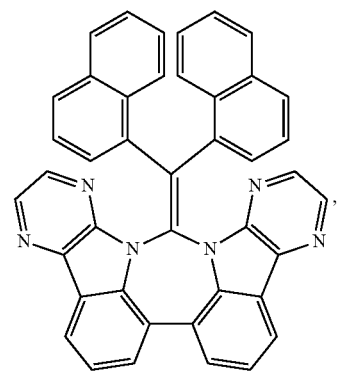 M7
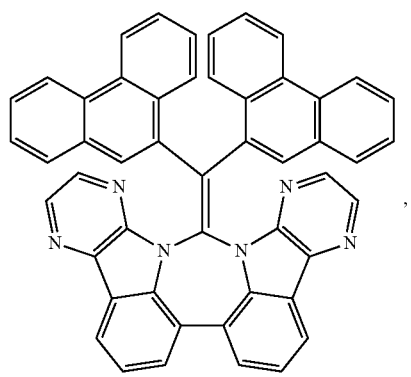 M8
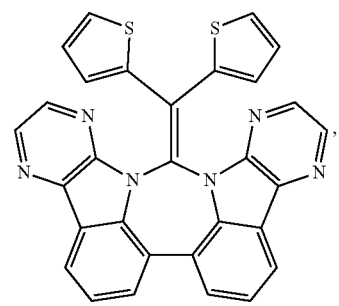 M9
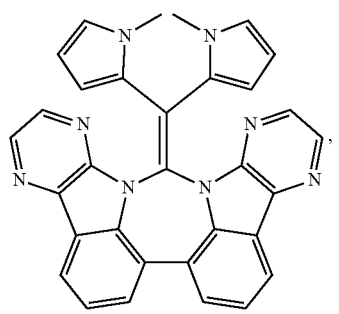 M10
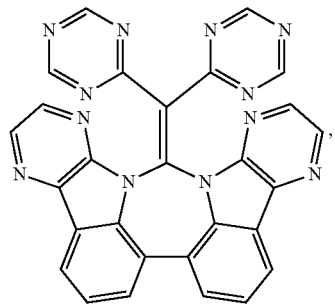 M11
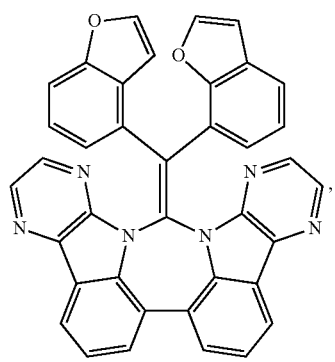 M12
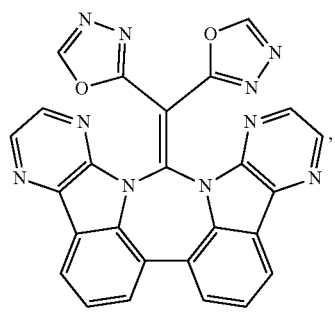 M13
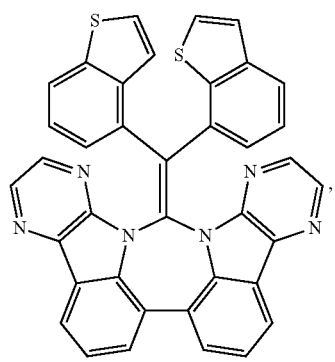 M14

M15
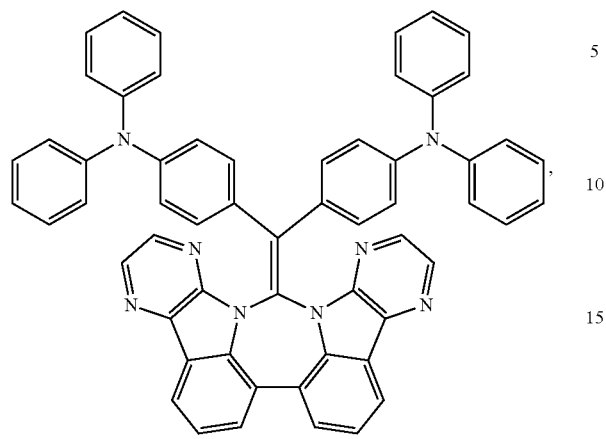
M16
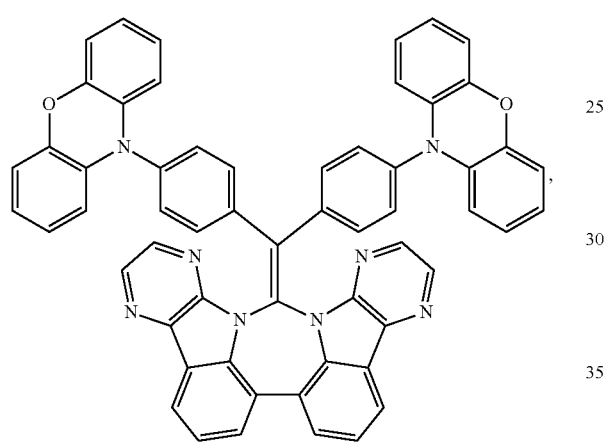
M17
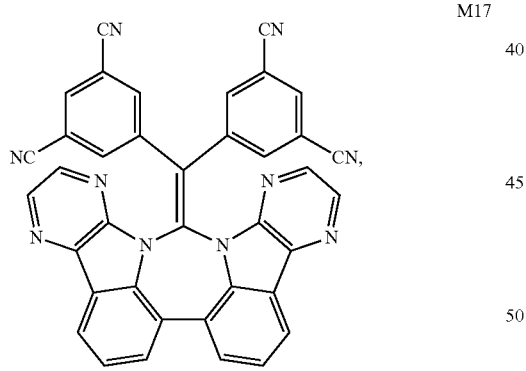
M18
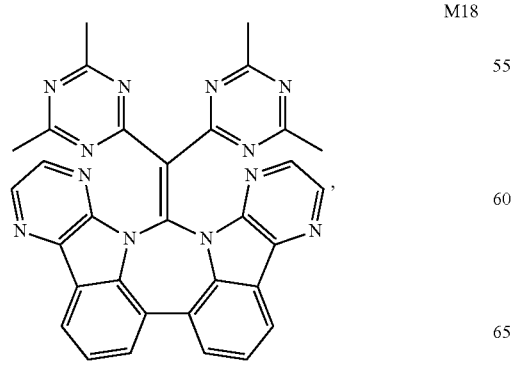
M19
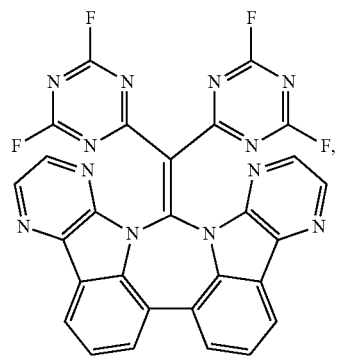
M20
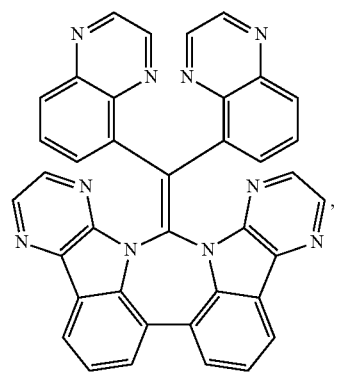
M21
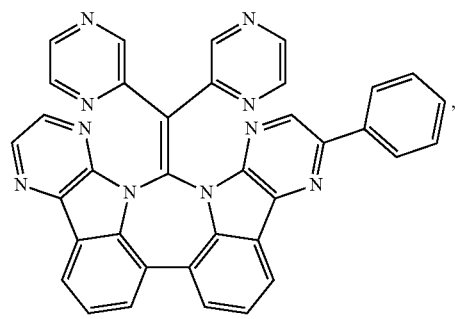
M22
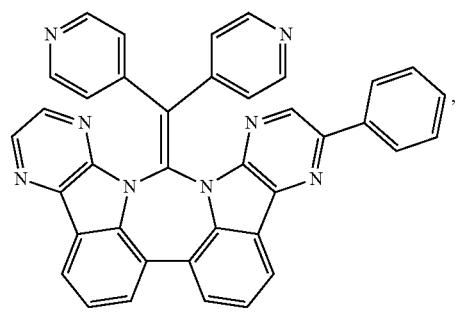

-continued
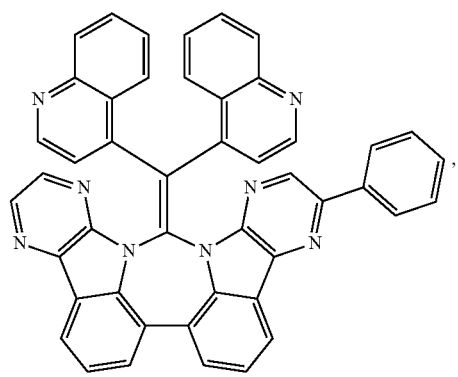
M23
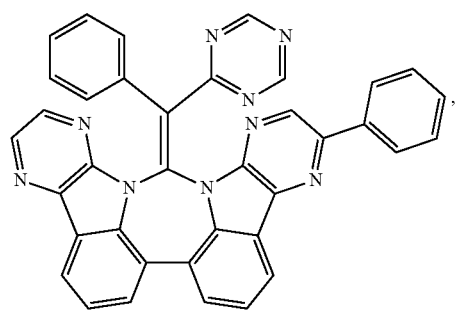
M24
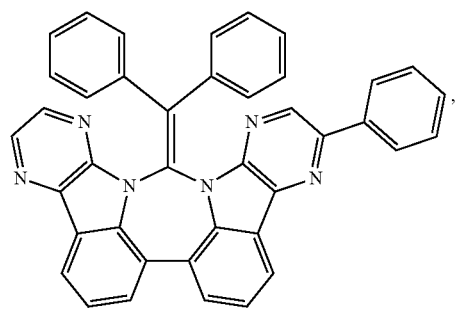
M25
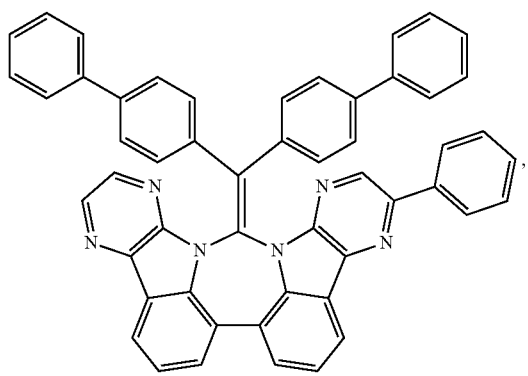
M26
-continued
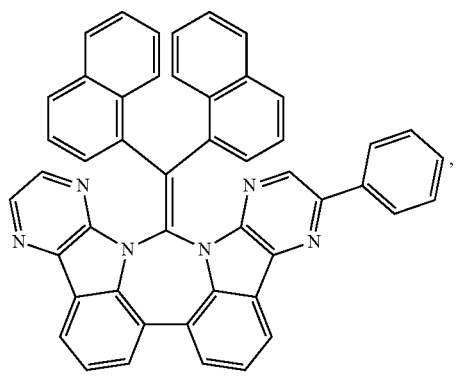
M27
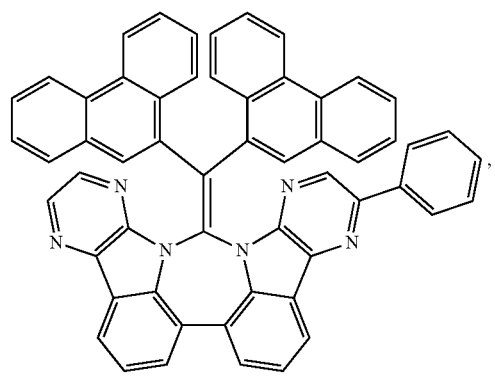
M28
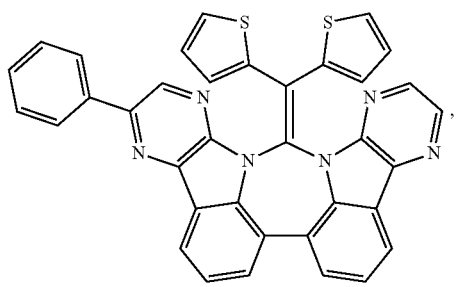
M29
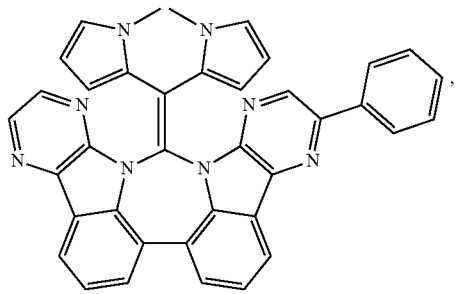
M30
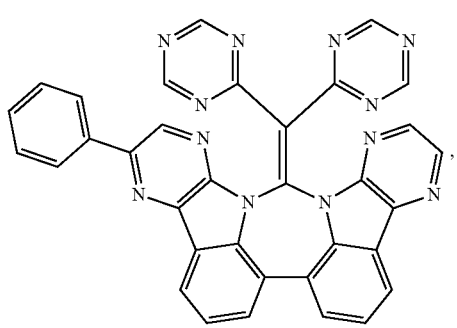
M31

-continued
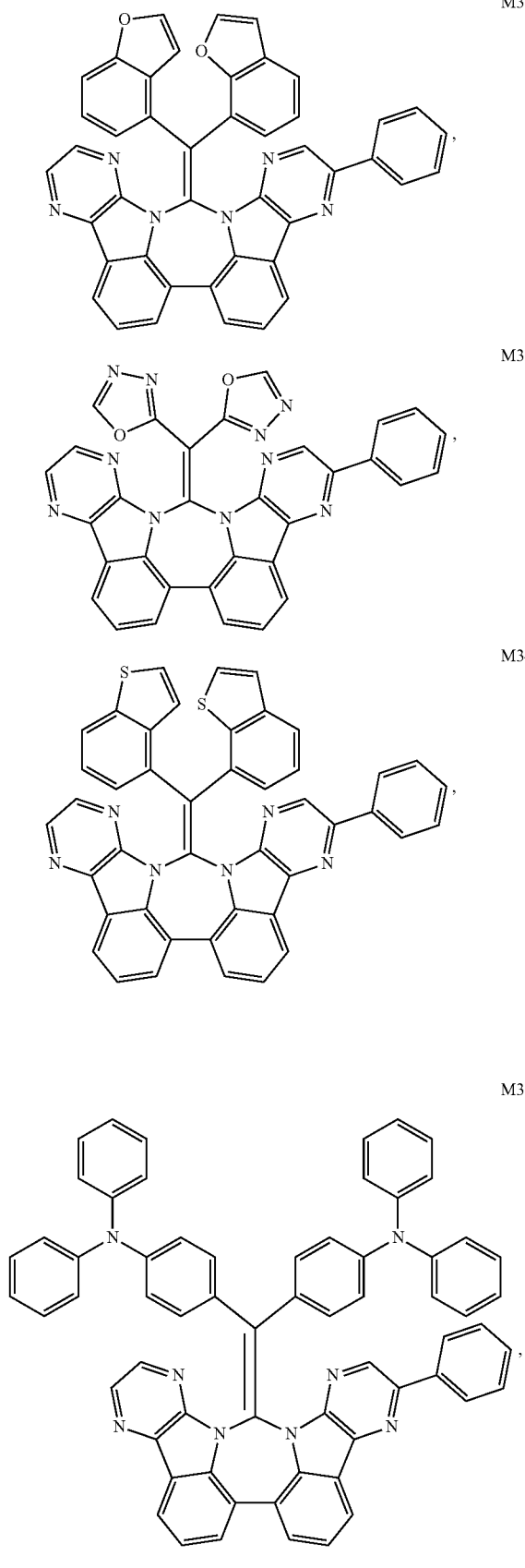
M32
M33
M34
M35
-continued
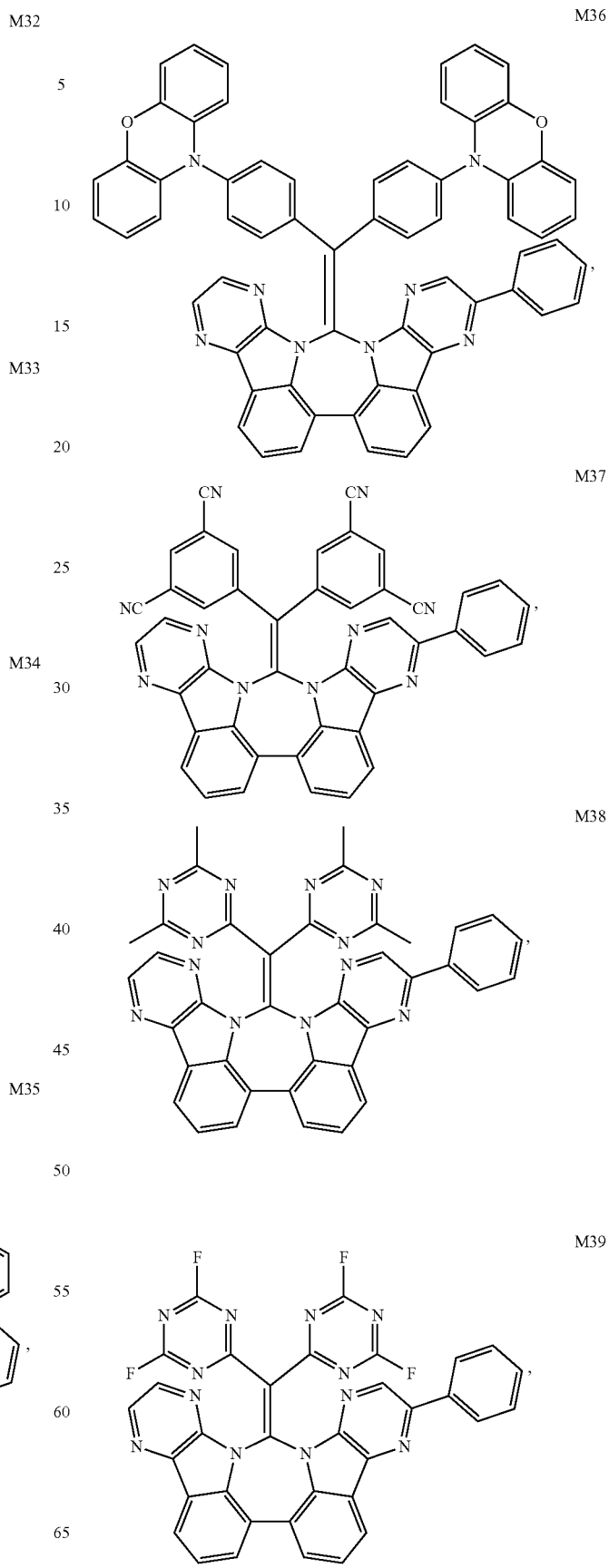
M36
M37
M38
M39

M40
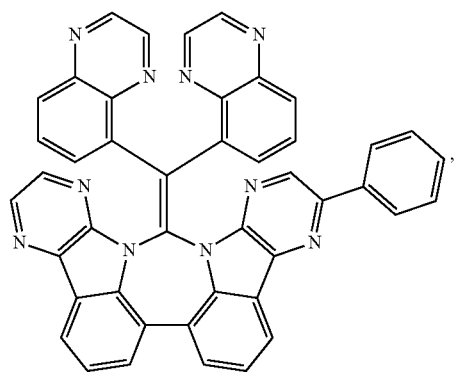
M41
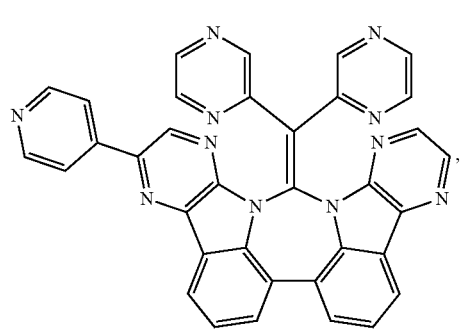
M42
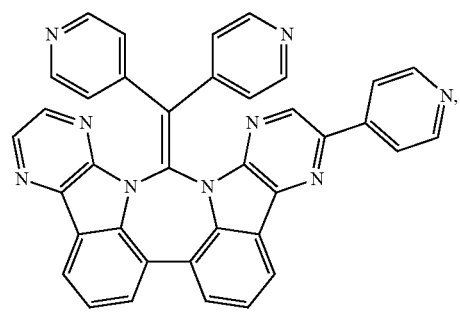
M43
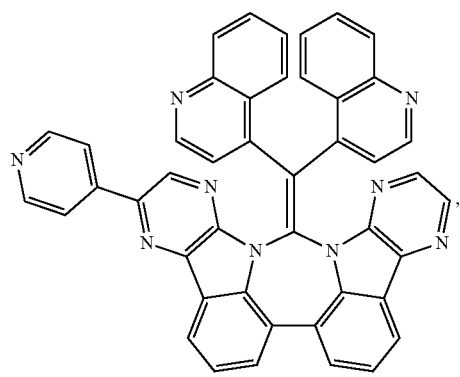
M44
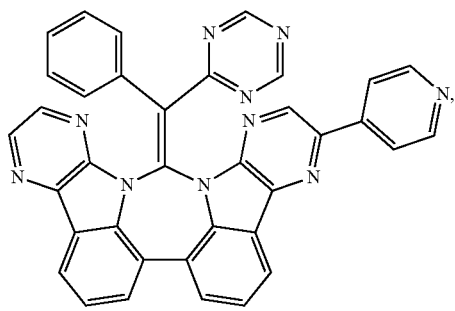
M45
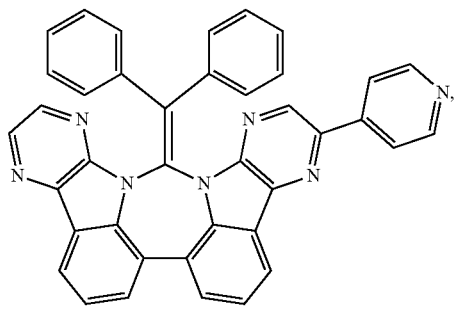
M46
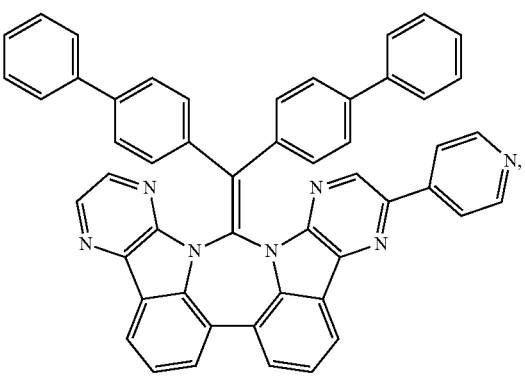
M47
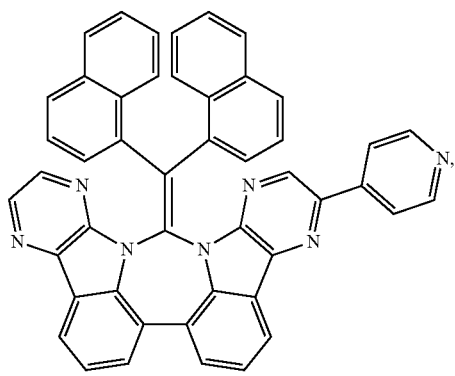

M48
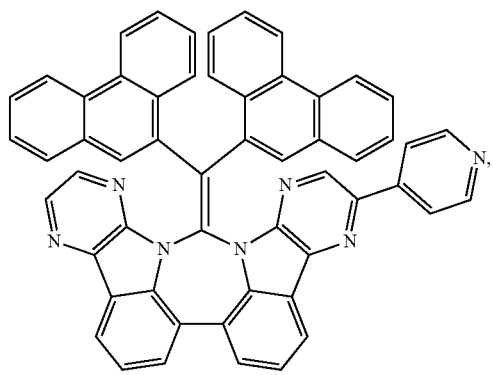
M49
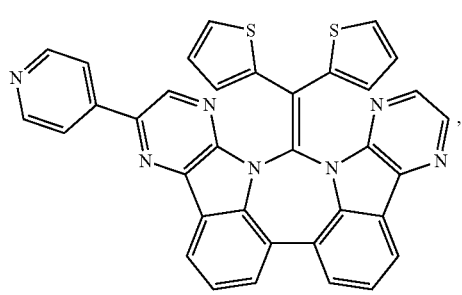
M50
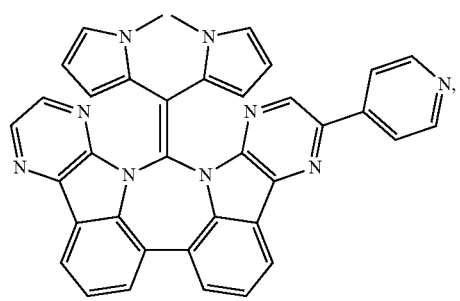
M51
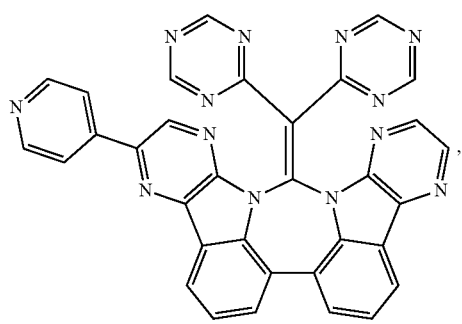
M52
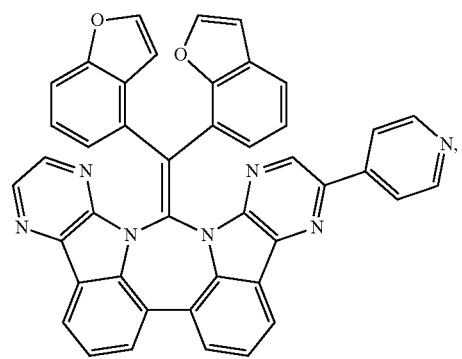
M53
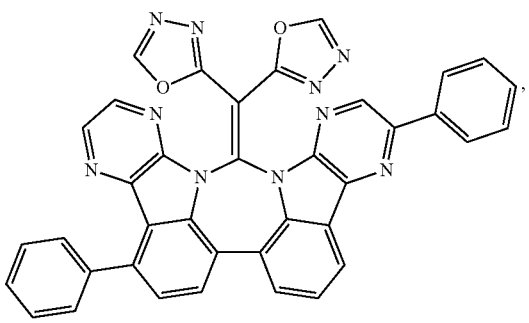
M54
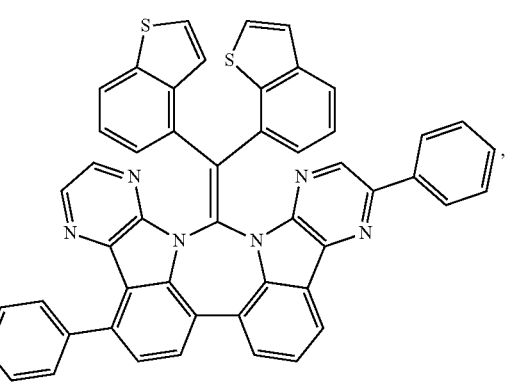
M55
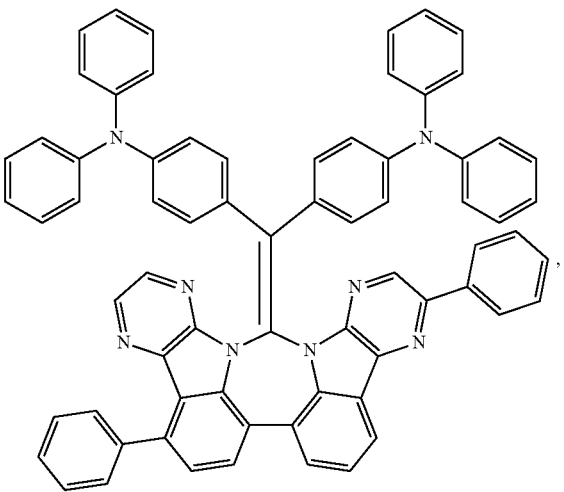

M56
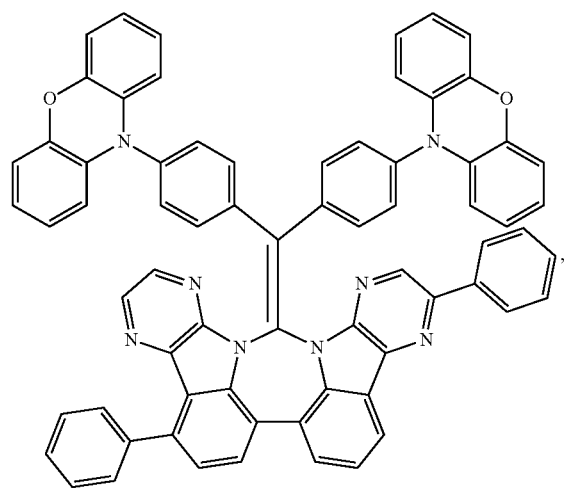
M57
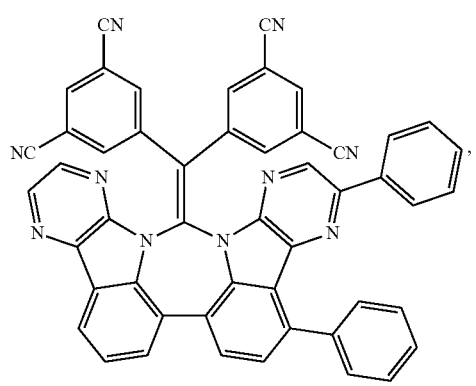
M58
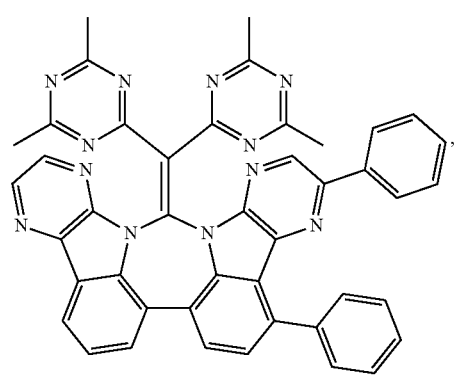
M59
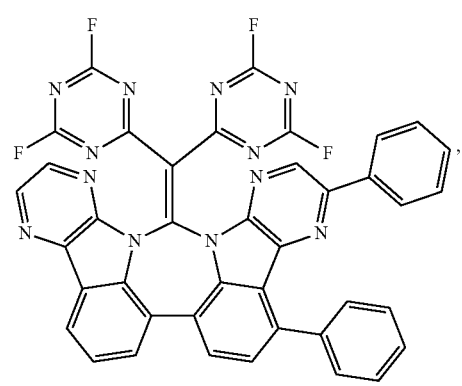
M60
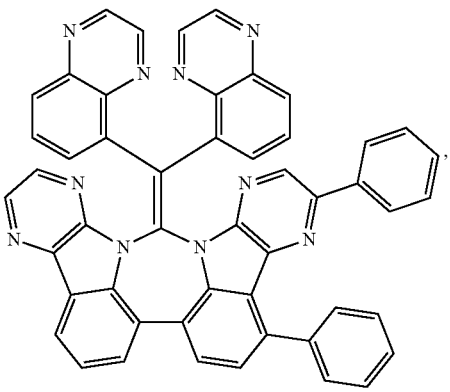
M61
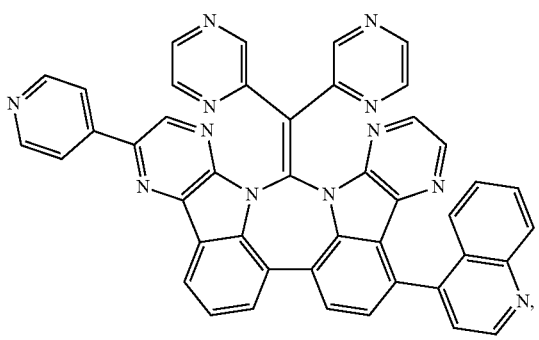
M62
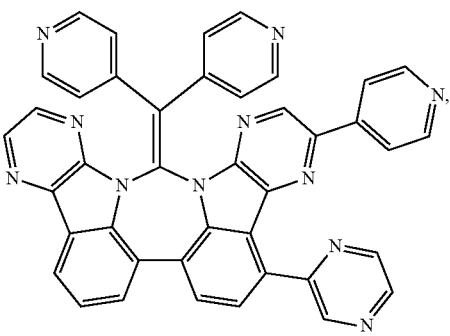
M63
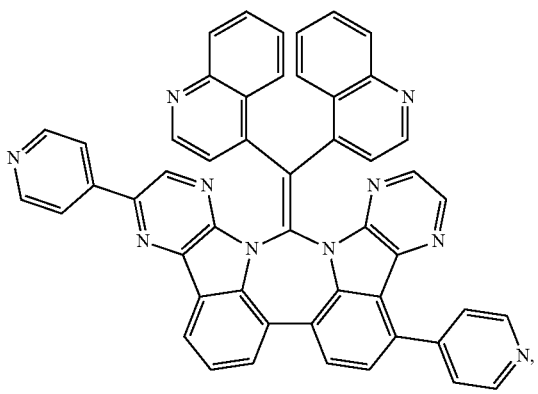

-continued
M64
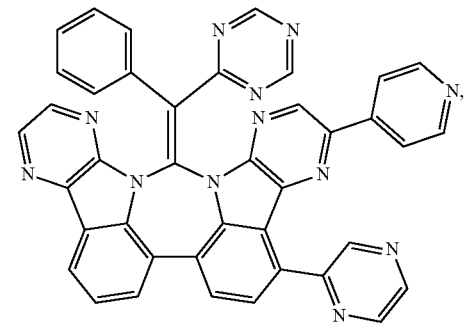
M65
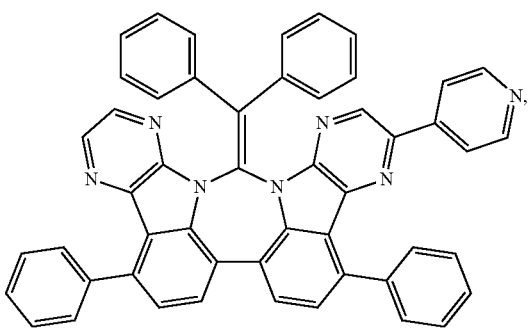
M66
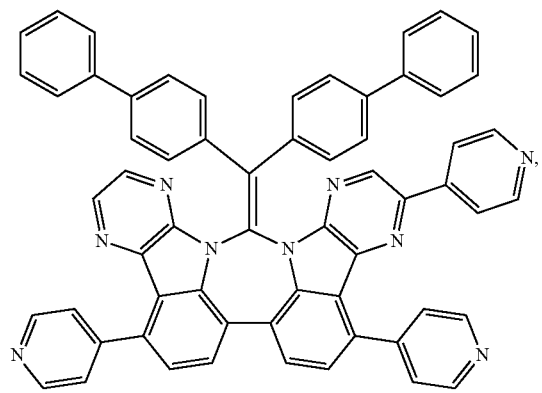
M67
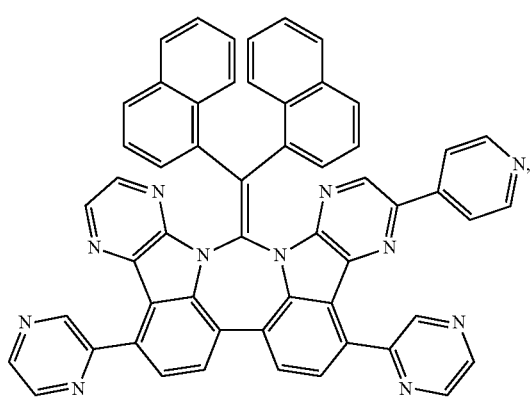
-continued
M68
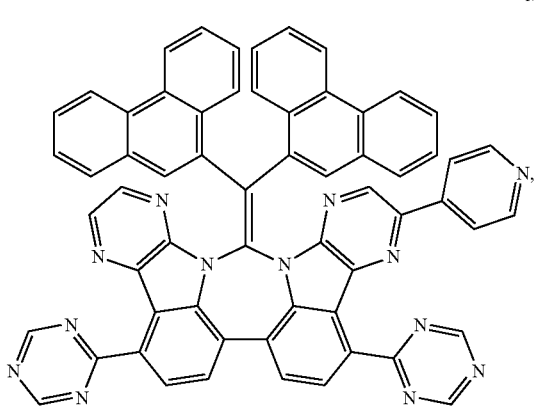
M69
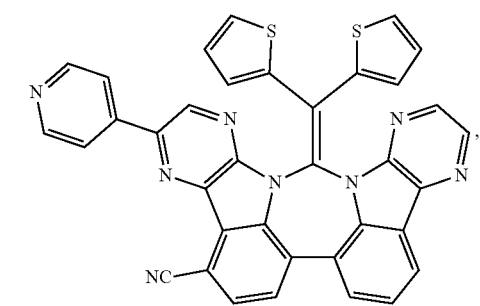
M70
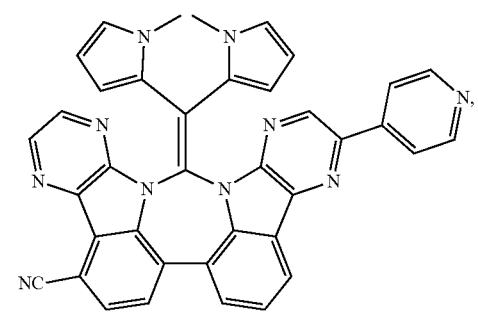
M71
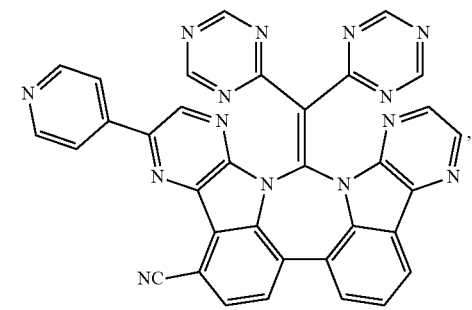

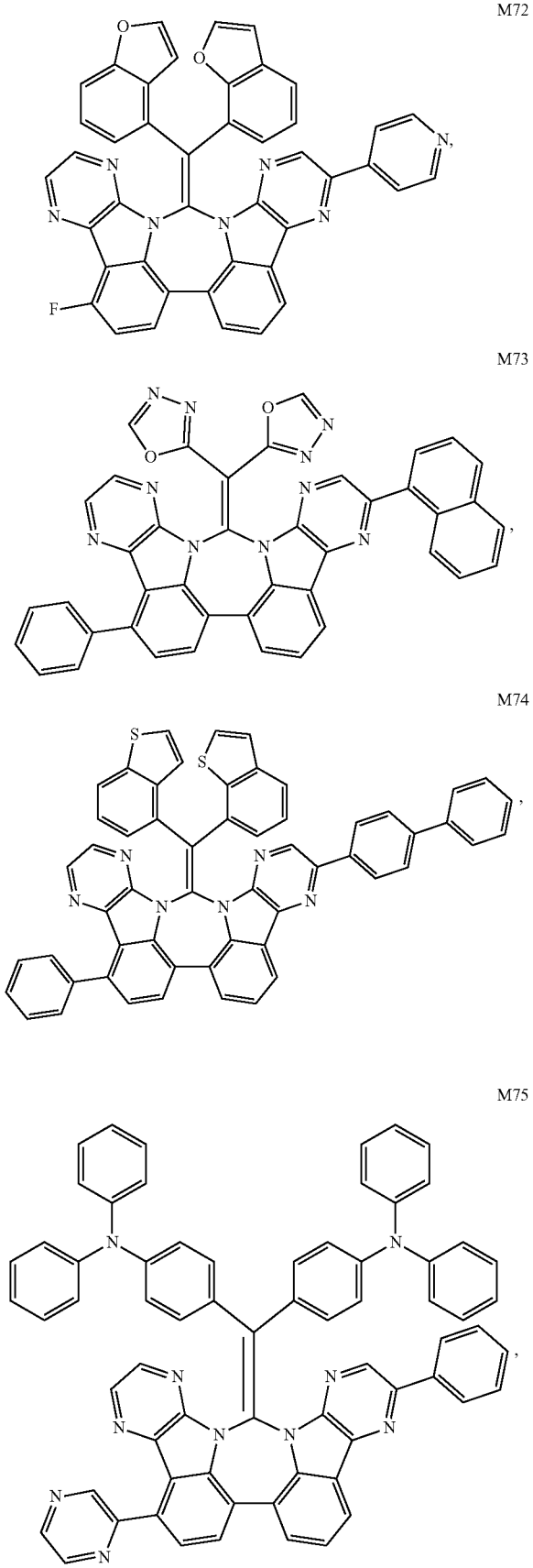
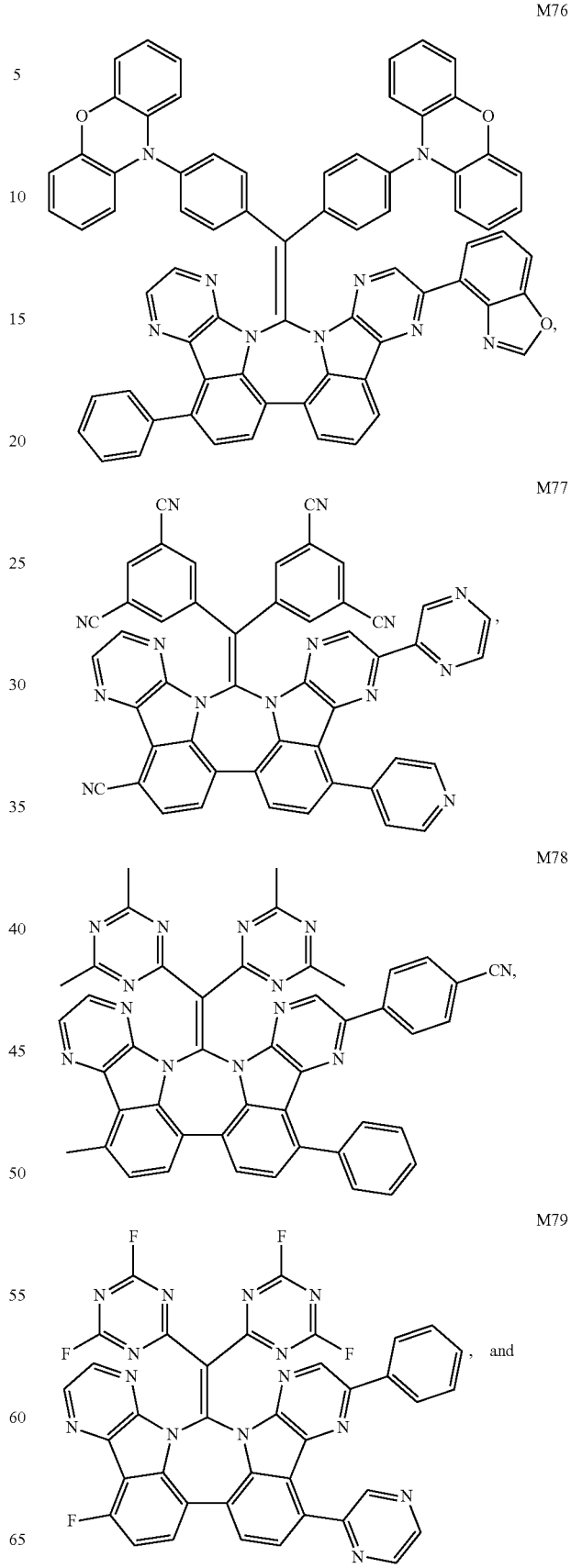

-continued

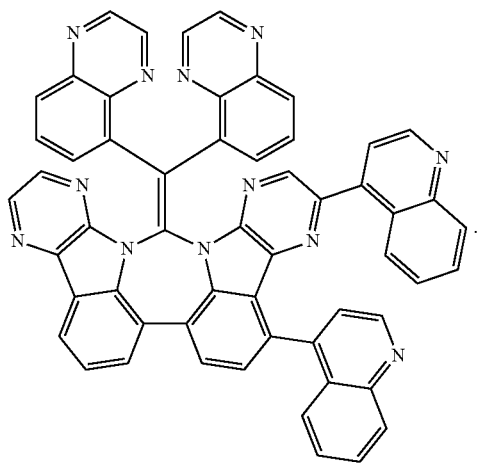

M80

The organic compound having a structure represented by Formula I in the present disclosure is exemplarily prepared according to the following synthesis route:

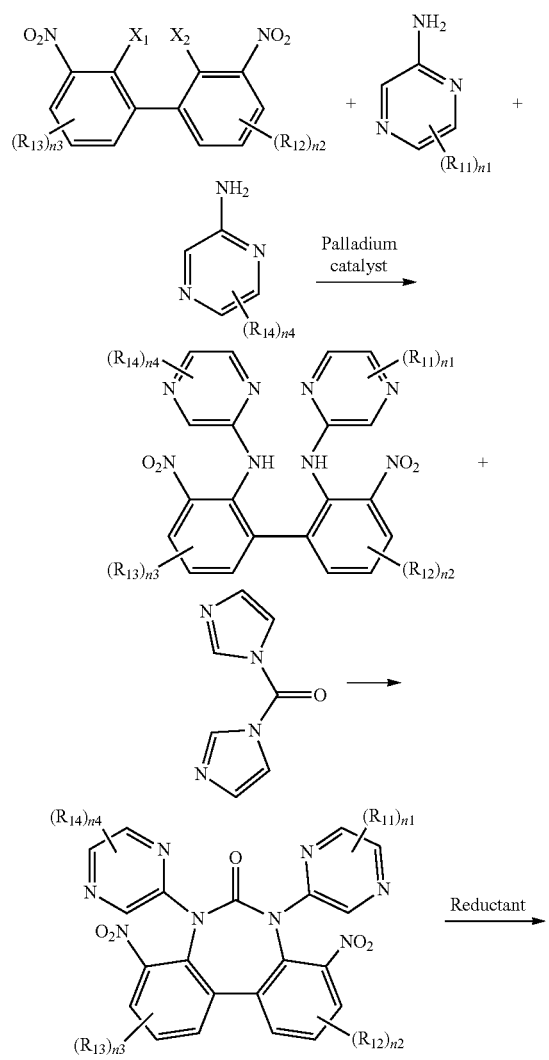

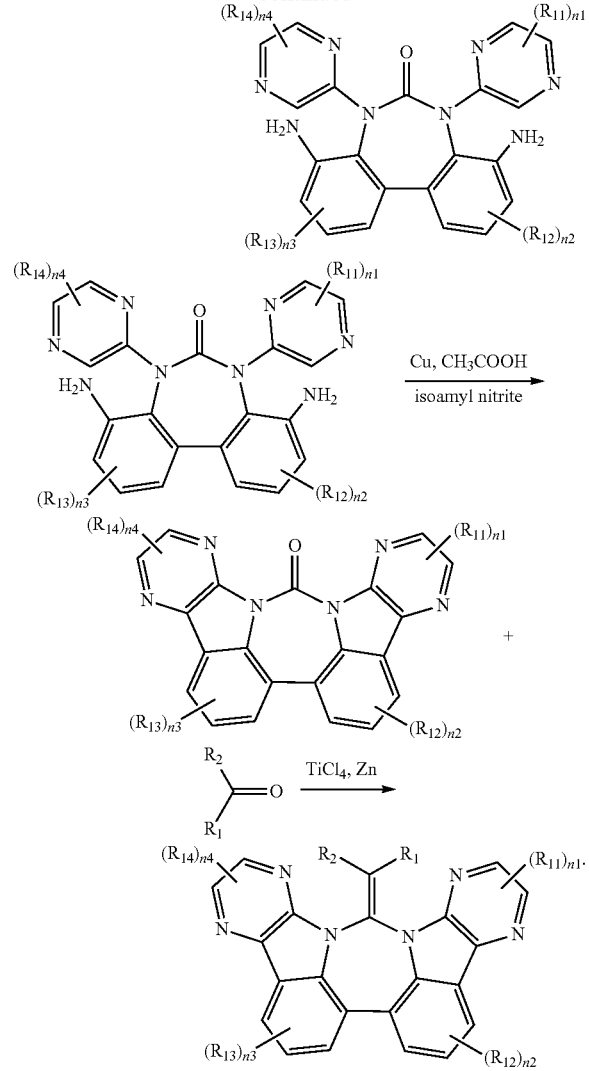

In the above synthesis route, $X_1$ and $X_2$ are each independently selected from halogen (such as fluorine, chlorine, bromine, or iodine), and $R_1$, $R_2$, $R_{11}$, $R_{12}$, $R_{13}$, $R_{14}$, $n_1$, $n_2$, $n_3$, and $n_4$ are each independently as defined in Formula I.

A second object of the present disclosure is to provide an electroluminescent material including the organic compound as described for the first object.

A third object of the present disclosure is to provide a display panel. The display panel includes an OLED device, the OLED device includes an anode, a cathode and an organic thin film layer disposed between the anode and the cathode, and a material of the organic thin film layer includes the electroluminescent material as described for the second object.

In an embodiment, the organic thin film layer includes a light emitting layer whose material includes the electroluminescent material as described for the second object.

In an embodiment, the electroluminescent material is used as a phosphorescent host material of the light emitting layer.

In an embodiment, the organic thin film layer further includes any one or a combination of at least two of a hole transport layer, a hole injection layer, an electron blocking layer, a hole blocking layer, an electron transport layer, and an electron injection layer.

In the OLED device of the present disclosure, a material of the anode may be a metal, a metal oxide, or a conductive polymer, where the metal includes copper, gold, silver, iron, chromium, nickel, manganese, palladium, and platinum, etc. as well as alloys thereof, the metal oxide includes indium tin oxide (ITO), indium zinc oxide (IZO), zinc oxide, and indium gallium zinc oxide (IGZO), etc., and the conductive polymer includes polyaniline, polypyrrole, and poly(3-methylthiophene), etc. In addition to the above materials that facilitate hole injection and combinations thereof, the material of the anode further includes known materials suitable for use as the anode.

In the OLED device, a material of the cathode may be a metal or a multilayer metal material, where the metal includes aluminum, magnesium, silver, indium, tin, and titanium, etc. as well as alloys thereof, and the multilayer metal material includes LiF/Al, LiO$_2$/Al, and BaF$_2$/Al, etc. In addition to the above materials that facilitate electron injection and combinations thereof, the material of the cathode further includes known materials suitable for use as the cathode.

In the OLED device, the organic thin film layer includes at least one light emitting layer (EML) and any one or a combination of at least two of a hole transport layer (HTL), a hole injection layer (HIL), an electron blocking layer (EBL), a hole blocking layer (HBL), an electron transport layer (ETL), and an electron injection layer (EIL) which is(are) disposed on two sides of the at least one light emitting layer, where the hole/electron injection and transport layers may include carbazole compounds, arylamine compounds, benzimidazole compounds, and metal compounds, etc. The OLED device may further be provided with a capping layer (CPL) disposed on the cathode (a side of the cathode facing away from the anode).

As shown in FIG. 1 which is a schematic diagram of the OLED device, the OLED device includes an anode 101, a cathode 102, and a light emitting layer 103 disposed between the anode 101 and the cathode 102, wherein a first organic thin film layer 104 and a second organic thin film layer 105 are disposed on two sides of the light emitting layer 103. The first organic thin film layer 104 is any one or a combination of at least two of a hole transport layer (HTL), a hole injection layer (HIL), or an electron blocking layer (EBL), and the second organic thin film layer 105 includes any one or a combination of at least two of an electron transport layer (ETL), a hole blocking layer (HBL), or an electron injection layer (EIL). A capping layer (CPL) may be further disposed on the cathode 102 (a side of the cathode 102 facing away from 105).

The OLED device may be prepared by the following method: forming the anode on a transparent or opaque smooth substrate, forming organic thin layers on the anode, and forming the cathode on the organic thin layers. The organic thin layers may be formed by using known film forming methods such as evaporation, sputtering, spin coating, impregnation, and ion plating.

A fourth object of the present disclosure is to provide an electronic apparatus including the display panel as described for the third object.

Examples of the organic compound of the present disclosure are illustratively listed below.

Example 1

This example provides an organic compound M1 having the following structure:

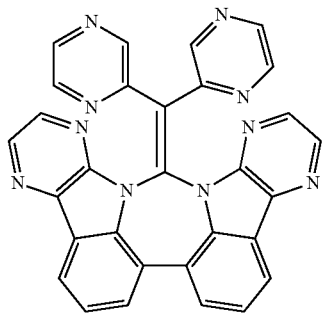

M1

A preparation method for the organic compound M1 includes steps described below.

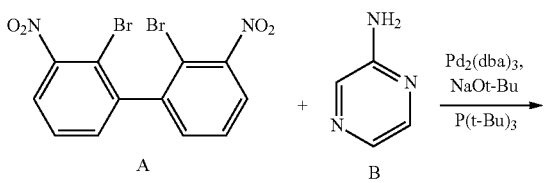

(1)

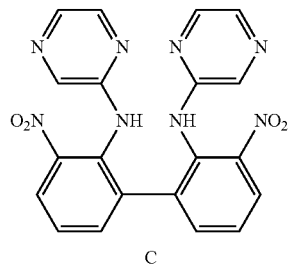

C

Compound A (4.02 g, 10 mmol), compound B (1.91 g, 20 mmol), 150 mL of toluene without water and oxygen, sodium t-butoxide (NaOt-Bu) (2.88 g, 30 mmol), tris(dibenzalacetone)dipalladium (Pd$_2$(dba)$_3$) (0.18 g, 0.2 mmol), and tri-t-butylphosphine P(t-Bu)$_3$ (0.1 mL of 10% toluene solution) were sequentially added to a 250 mL three-necked flask and reacted at 120° C. for 24 h under a nitrogen atmosphere. The reaction solution was cooled to room temperature, poured into 200 mL of iced water, and extracted three times with dichloromethane. The organic phases were combined, spun into silica gel, and separated and purified through column chromatography (the mobile phase was a mixed solution of dichloromethane and n-hexane at a volume ratio of 1:1) to obtain compound C.

Characterization Results of Compound C:

$^1$H-NMR (400 MHz, CDCl$_3$): δ 8.30 (d, J=7.5 Hz, 2H), 8.20-8.08 (m, 4H), 7.94 (s, 2H), 7.67 (dd, J=7.5, 1.5 Hz, 1H), 7.38 (t, J=7.5 Hz, 2H), 5.90 (d, J=6.8 Hz, 2H);

$^{13}$C-NMR (100 MHz, CDCl$_3$): δ 150.59, 144.18 (dd, J=8.3, 1.2 Hz), 138.34, 136.49 (t, J=8.7 Hz), 134.80-133.80 (m), 132.88 (ddd, J=20.5, 8.2, 1.7 Hz), 127.58, 126.02-124.89 (m), 122.37 (tt, J=4.0, 2.2 Hz).

(2)

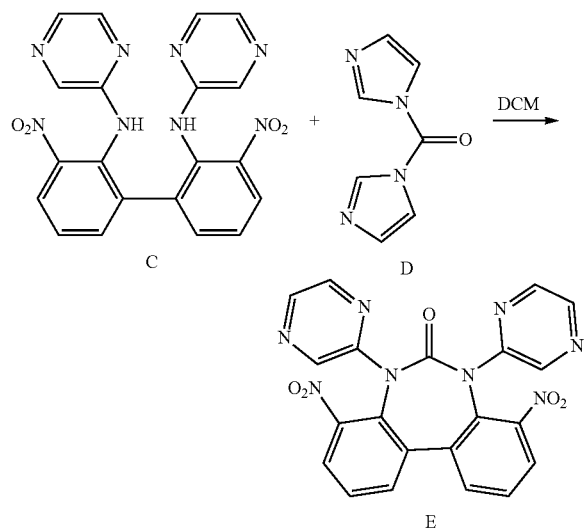

Compound C obtained in step (1) (8.61 g, 20 mmol) and 100 mL of dichloromethane (DCM) were sequentially added to a 250 mL three-necked flask. A mixed solution of compound D (N, N'-carbonyldiimidazole) (4.05 g, 25 mmol) and 100 mL of dichloromethane was added dropwise at room temperature. After the addition, the mixture was reacted at room temperature for 2 h and then filtered with suction. A filter cake was rinsed with dichloromethane to obtain compound E.

Characterization Results of Compound E:
$^1$H-NMR (400 MHz, CDCl$_3$): δ 8.40-8.29 (m, 4H), 8.24 (dd, J=7.5, 1.5 Hz, 2H), 8.07 (s, 2H), 7.75 (dd, J=7.4, 1.5 Hz, 2H), 7.32 (t, J=7.5 Hz, 2H);
$^{13}$C-NMR (100 MHz, CDCl$_3$): δ 152.12, 146.42, 145.28 (dd, J=8.3, 1.2 Hz), 143.86-143.01 (m), 137.89 (dd, J=9.1, 1.2 Hz), 137.16, 136.85-136.39 (m), 131.56 (dd, J=7.2, 2.1 Hz), 127.68, 124.96 (tt, J=4.1, 2.1 Hz), 124.49 (dd, J=7.3, 2.1 Hz).

(3)

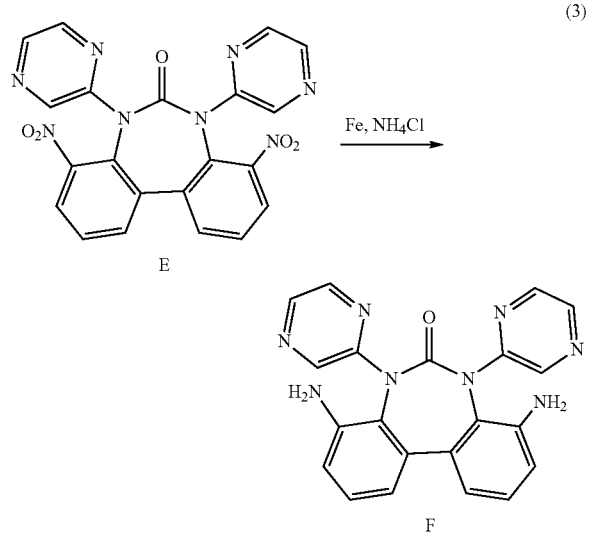

Compound E obtained in step (2) (9.13 g, 20 mmol), 1000 mL of ethanol, iron powder (4.3 g, 1 mol), and 100 mL of saturated aqueous ammonium chloride solution were sequentially added into a 250 mL three-necked flask, and heated and refluxed for 5 h. After TLC monitored that the reaction was complete, the reaction solution was filtered, and a filter cake was rinsed with ethyl acetate. After the filtrate was separated, the organic phases were spin-dried to obtain compound F.

Characterization Results of Compound F:
$^1$H-NMR (400 MHz, CDCl$_3$): δ 8.48-8.21 (m, 4H), 8.07 (s, 2H), 7.71 (dd, J=7.5, 1.5 Hz, 2H), 7.15 (t, J=7.5 Hz, 2H), 6.76 (dd, J=7.5, 1.5 Hz, 2H), 5.40 (s, 4H);
$^{13}$C-NMR (100 MHz, CDCl$_3$): δ 153.25, 148.28, 145.22 (dd, J=8.4, 1.2 Hz), 144.57-143.89 (m), 138.14 (dd, J=9.1, 1.2 Hz), 137.65-134.89 (m), 130.71, 128.02 (tt, J=4.1, 2.1 Hz), 125.99, 120.25 (dd, J=7.2, 2.1 Hz), 117.22-114.67 (m).

(4)

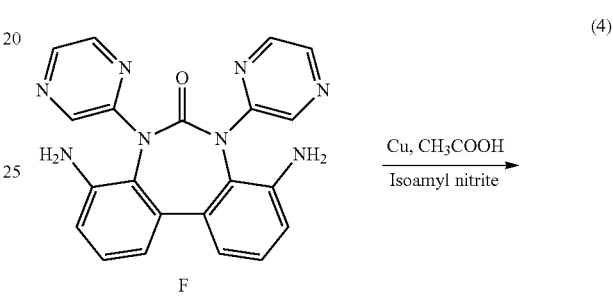

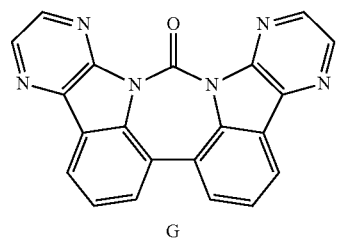

In a 1000 mL three-necked flask, compound F obtained in step (3) (7.92 g, 20 mmol) was dissolved in 32 mL of acetic acid, and copper powder (2 g) was added, stirred, and cooled to 5° C. Isoamyl nitrite (7.8 g, 66 mmol) was dissolved in 16 mL of acetic acid and slowly added dropwise to the system. After the dropwise addition, the mixture was stirred at room temperature. After TLC monitored that the reaction was complete, the reaction solution was separated, and the organic phases were washed once with an aqueous sodium carbonate solution, dried with anhydrous sodium sulfate, spin-dried, and subjected to column chromatography (the eluent was dichloromethane/petroleum ether) to obtain compound G.

Characterization Results of Compound G:
$^1$H-NMR (400 MHz, CDCl$_3$): δ 8.81 (dd, J=7.5, 1.5 Hz, 2H), 8.67 (d, J=7.5 Hz, 2H), 8.43 (d, J=7.5 Hz, 2H), 7.93 (dd, J=7.5, 1.5 Hz, 2H), 7.62 (t, J=7.5 Hz, 2H);
$^{13}$C-NMR (100 MHz, CDCl$_3$): δ 154.48, 146.82, 141.73 (d, J=8.3 Hz), 138.34-136.90 (m), 134.74 (dd, J=6.5, 1.2 Hz), 126.82 (dd, J=7.0, 2.1 Hz), 125.32-123.19 (m), 116.42, 114.79-113.29 (m).

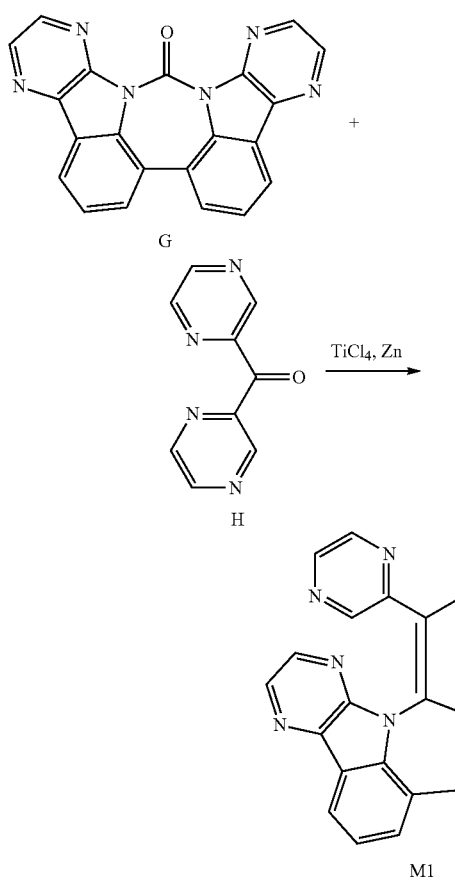

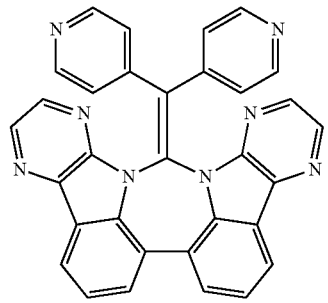

In an Ar atmosphere, zinc powder (1.6 g, 24 mmol) and 40 mL of tetrahydrofuran (THF) were added to a three-necked flask equipped with a magnetic stirrer. The mixture was cooled to −5° C., TiCl₄ (1.3 mL, 12 mmol) was slowly added with a syringe, and the system was kept below 10° C. The suspended mixture was heated to room temperature and stirred for 0.5 h and then heated to reflux for 2.5 h. Compound G obtained in step (4) (7.25 g, 20 mmol) and compound H (3.72 g, 20 mmol) were dissolved in 15 mL of THF and then slowly added dropwise to the suspended mixture. After the addition, the reaction mixture was heated to reflux until the carbonyl compound was consumed (monitored through thin-layer chromatography (TLC)) (about 14 h). The reaction was cooled, quenched with 10% aqueous K₂CO₃ solution, and extracted with CH₂Cl₂. The organic layer was collected and concentrated, and the crude matter was purified through flash chromatography to obtain the target product M1.

Characterization Results of the Organic Compound M1:

¹H-NMR (400 MHz, CDCl₃): δ 8.77 (dd, J=7.5, 1.5 Hz, 2H), 8.75 (d, J=7.5 Hz, 2H), 8.70 (d, J=7.5 Hz, 2H), 8.66 (s, 2H), 8.50 (d, J=7.5 Hz, 2H), 8.30 (d, J=7.5 Hz, 2H), 7.91 (dd, J=7.5, 1.6 Hz, 2H), 7.63 (t, J=7.5 Hz, 2H);

¹³C-NMR (100 MHz, CDCl₃): δ 147.62, 146.60-145.21 (m), 143.98-142.99 (m), 142.36, 141.84 (dd, J=9.3, 1.0 Hz), 139.75-138.66 (m), 137.41 (d, J=8.3 Hz), 130.90 (dd, J=6.7, 1.2 Hz), 126.74 (dd, J=7.0, 2.0 Hz), 122.90 (tq, J=3.4, 1.8 Hz), 121.90 (td, J=6.4, 2.0 Hz), 118.13, 115.84-114.87 (m), 114.27.

Example 2

This example provides an organic compound M2 having the following structure:

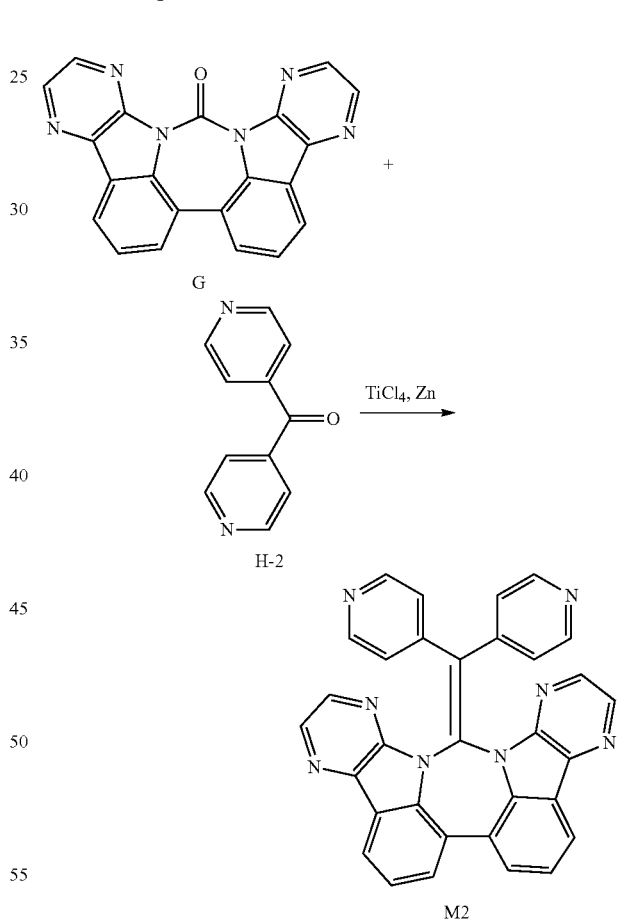

A preparation method for the organic compound M2 includes steps described below.

In an Ar atmosphere, zinc powder (1.6 g, 24 mmol) and 40 mL of THF were added to a three-necked flask equipped with a magnetic stirrer. The mixture was cooled to −5° C., TiCl₄ (1.3 mL, 12 mmol) was slowly added with a syringe, and the system was kept below 10° C. The suspended mixture was heated to room temperature and stirred for 0.5 h and then heated to reflux for 2.5 h. Compound G (7.25 g, 20 mmol) whose preparation method was the same as that of Example 1 and compound H-2 (3.69 g, 20 mmol) were dissolved in 15 mL of THF and then slowly added dropwise to the suspended mixture. After the addition, the reaction mixture was heated to reflux until the carbonyl compound was consumed (monitored by thin-layer chromatography (TLC)) (about 14 h). The reaction was cooled, quenched with 10% aqueous $K_2CO_3$ solution, and extracted with $CH_2Cl_2$. The organic layer was collected and concentrated, and the crude matter was purified through flash chromatography to obtain the target product M2.

Characterization Results of the Organic Compound M2:

$^1$H-NMR (400 MHz, CDCl$_3$): δ 8.77 (dd, J=7.5, 1.5 Hz, 2H), 8.70 (d, J=7.5 Hz, 2H), 8.58-8.53 (m, 4H), 8.31 (d, J=7.5 Hz, 2H), 7.90 (dd, J=7.5, 1.5 Hz, 2H), 7.63 (t, J=7.5 Hz, 2H), 7.46-7.41 (m, 4H);

$^{13}$C-NMR (100 MHz, CDCl$_3$): δ 147.79, 147.78, 147.73, 147.72, 147.65, 147.16, 139.23, 139.16, 138.07, 138.02, 137.44, 137.38, 130.93, 130.92, 130.88, 130.87, 126.77, 126.76, 126.72, 126.70, 122.92, 122.90, 122.89, 122.87, 121.91, 121.90, 121.33, 121.32, 121.27, 121.26, 119.92, 117.40, 115.53.

Example 3

This example provides an organic compound M3 having the following structure:

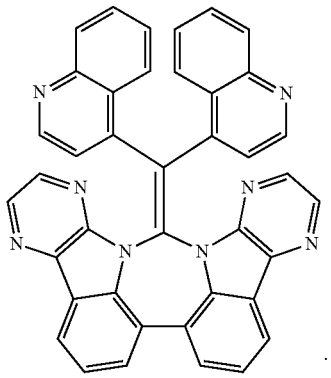

M3

A preparation method for the organic compound M3 includes steps described below.

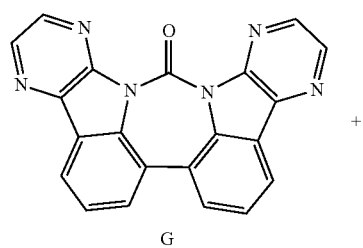

G

+

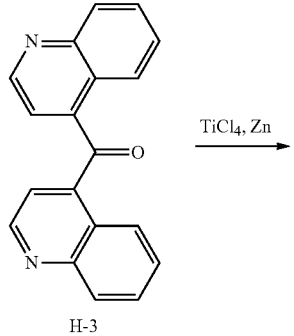

H-3

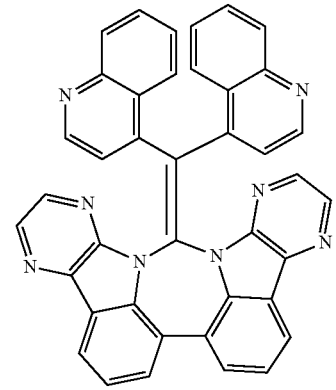

M3

In an Ar atmosphere, zinc powder (1.6 g, 24 mmol) and 40 mL of THF were added to a three-necked flask equipped with a magnetic stirrer. The mixture was cooled to −5° C., TiCl$_4$ (1.3 mL, 12 mmol) was slowly added with a syringe, and the system was kept below 10° C. The suspended mixture was heated to room temperature and stirred for 0.5 h and then heated to reflux for 2.5 h. Compound G (7.25 g, 20 mmol) whose preparation method was the same as that of Example 1 and compound H-3 (5.69 g, 20 mmol) were dissolved in 15 mL of THF and then slowly added dropwise to the suspended mixture. After the addition, the reaction mixture was heated to reflux until the carbonyl compound was consumed (monitored through thin-layer chromatography (TLC)) (about 14 h). The reaction was cooled, quenched with 10% aqueous $K_2CO_3$ solution, and extracted with $CH_2Cl_2$. The organic layer was collected and concentrated, and the crude matter was purified through flash chromatography to obtain the target product M3.

Characterization Results of the Organic Compound M3:

$^1$H-NMR (400 MHz, CDCl$_3$): δ 8.77 (dd, J=7.5, 1.5 Hz, 2H), 8.70 (d, J=7.5 Hz, 2H), 8.64 (d, J=7.5 Hz, 2H), 8.31 (d, J=7.5 Hz, 2H), 8.09 (dd, J=7.4, 1.5 Hz, 2H), 7.90 (dd, J=7.5, 1.5 Hz, 2H), 7.74 (td, J=7.4, 1.6 Hz, 2H), 7.67-7.60 (m, 4H), 7.60 (td, J=7.4, 1.5 Hz, 2H), 7.43 (d, J=7.5 Hz, 2H);

$^{13}$C-NMR (100 MHz, CDCl$_3$): δ 147.74, 147.17, 146.68, 146.65, 146.64, 146.61, 146.59, 146.58, 146.55, 144.38, 139.23, 139.16, 137.91, 137.45, 137.39, 134.53, 131.09, 131.08, 131.04, 131.03, 129.99, 129.97, 129.96, 129.93, 129.91, 129.89, 128.69, 128.68, 128.63, 128.62, 128.62, 126.83, 126.81, 126.77, 126.76, 126.64, 126.62, 124.54, 124.53, 124.52, 124.48, 124.46, 124.17, 124.16, 124.14, 124.11, 124.09, 124.08, 123.32, 123.31, 123.30, 123.28, 121.86, 121.84, 121.80, 121.78, 121.75, 121.73, 117.30, 116.35, 116.33, 116.32, 116.29, 116.27, 116.26, 116.23, 116.20, 113.05.

Example 4

This example provides an organic compound M4 having the following structure:

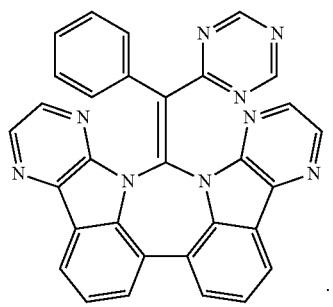

M4

A preparation method for the organic compound M4 includes steps described below.

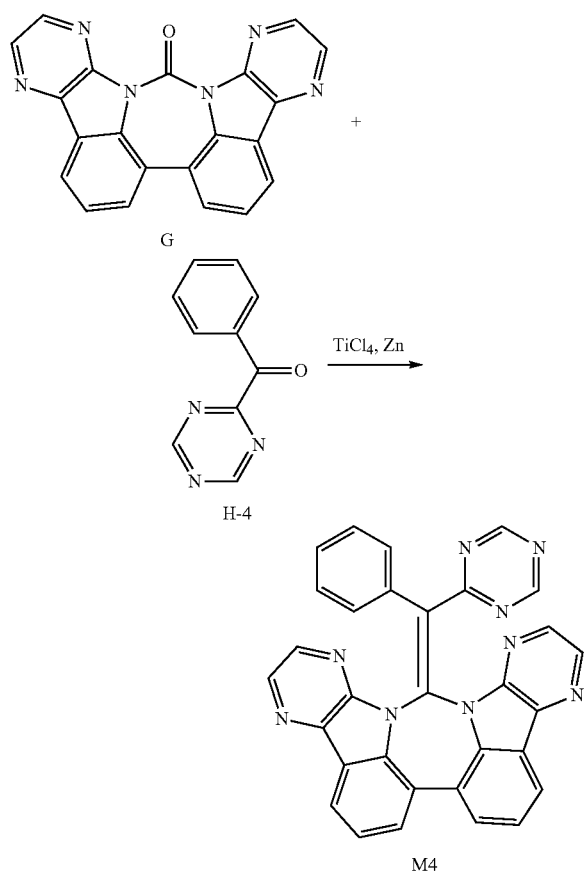

In an Ar atmosphere, zinc powder (1.6 g, 24 mmol) and 40 mL of THF were added to a three-necked flask equipped with a magnetic stirrer. The mixture was cooled to −5° C., TiCl$_4$ (1.3 mL, 12 mmol) was slowly added with a syringe, and the system was kept below 10° C. The suspended mixture was heated to room temperature and stirred for 0.5 h and then heated to reflux for 2.5 h. Compound G (7.25 g, 20 mmol) whose preparation method was the same as that of Example 1 and compound H-4 (3.71 g, 20 mmol) were dissolved in 15 mL of THF and then slowly added dropwise to the suspended mixture. After the addition, the reaction mixture was heated to reflux until the carbonyl compound was consumed (monitored through thin-layer chromatography (TLC)) (about 14 h). The reaction was cooled, quenched with 10% aqueous K$_2$CO$_3$ solution, and extracted with CH$_2$Cl$_2$. The organic layer was collected and concentrated, and the crude matter was purified through flash chromatography to obtain the target product M4.

Characterization Results of the Organic Compound M4:

$^1$H-NMR (400 MHz, CDCl$_3$): δ 8.77 (dd, J=7.5, 1.5 Hz, 2H), 8.70 (d, J=7.5 Hz, 2H), 8.30 (d, J=7.5 Hz, 2H), 8.16 (s, 2H), 7.91 (dd, J=7.5, 1.6 Hz, 2H), 7.63 (t, J=7.5 Hz, 2H), 7.39-7.29 (m, 3H), 7.31-7.24 (m, 2H);

$^{13}$C-NMR (100 MHz, CDCl$_3$): δ 163.68, 163.40, 150.56, 147.62, 139.23, 139.16, 139.01, 137.44, 137.38, 133.64, 130.93, 130.92, 130.88, 130.87, 129.59, 129.58, 129.57, 129.56, 128.16, 126.77, 126.76, 126.72, 126.70, 123.64, 123.62, 123.58, 123.56, 123.02, 122.93, 122.92, 122.90, 122.89, 122.87, 121.91, 121.90, 121.86, 121.84, 118.13, 115.33, 115.29.

The following are several examples of applications of the organic compounds of the present disclosure in OLED elements.

Application Example 1

This application example provides an OLED device. The OLED device includes a substrate, an indium tin oxide (ITO) anode with a thickness of 15 nm, a hole injection layer with a thickness of 10 nm, a hole transport layer with a thickness of 110 nm, a light emitting layer with a thickness of 30 nm, a first electron transport layer with a thickness of 30 nm, a second electron transport layer with a thickness of 5 nm, a cathode (a magnesium-silver electrode at a Mg—Ag mass ratio of 9:1) with a thickness of 15 nm, and a capping layer with a thickness of 100 nm.

The OLED Device was Prepared by Steps Described Below.

(1) A glass substrate with a size of 50 mm×50 mm×0.7 mm was cut, sonicated in isopropyl alcohol and deionized water for 30 min separately, and cleaned under ozone for 10 min. The obtained glass substrate having the ITO anode with a thickness of 15 nm was installed onto a vacuum deposition apparatus.

(2) A compound HAT-CN was deposited through vacuum evaporation on the ITO anode layer at a vacuum degree of 2×10$^{-6}$ Pa as the hole injection layer with a thickness of 10 nm.

(3) A compound TAPC was deposited through vacuum evaporation on the hole injection layer as the hole transport layer with a thickness of 110 nm.

(4) The light emitting layer with a thickness of 30 nm was co-deposited on the hole transport layer, where the organic compound M1 provided in Example 1 of the present disclosure was used as a host material of the light emitting layer, a compound Ir(piq)$_2$(acac) was used as a doped material of the light emitting layer, and a mass ratio of M1 to the doped material was 9:1.

(5) A compound TPBi was deposited through vacuum evaporation on the light emitting layer as the first electron transport layer with a thickness of 30 nm.

(6) A compound Alq3 was deposited through vacuum evaporation on the first electron transport layer as the second electron transport layer with a thickness of 5 nm.

(7) The magnesium-silver electrode was deposited through vacuum evaporation on the second electron transport layer as the cathode with a thickness of 15 nm.

(8) CBP was deposited through vacuum evaporation on the cathode as a cathode covering layer (the capping layer) with a thickness of 100 nm.

The Compounds Used in the OLED Device have the Following Structures:

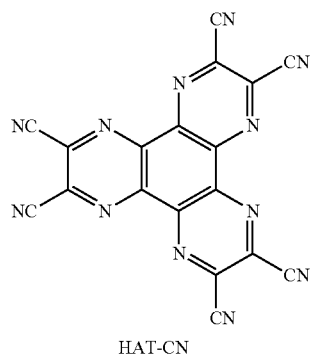

HAT-CN

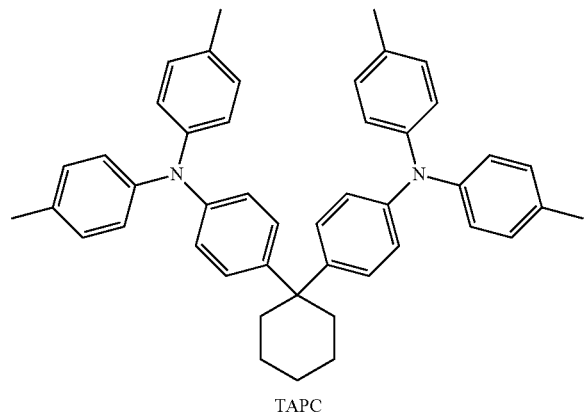

TAPC

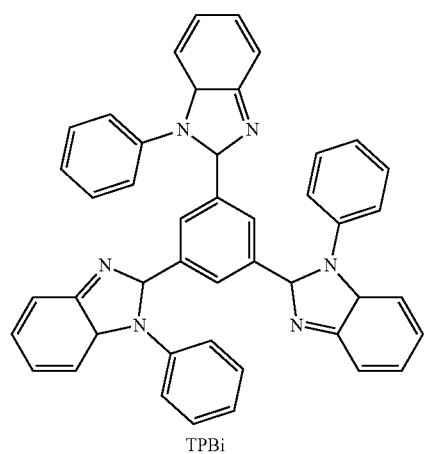

TPBi

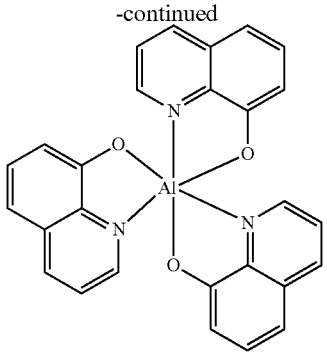

Alq3

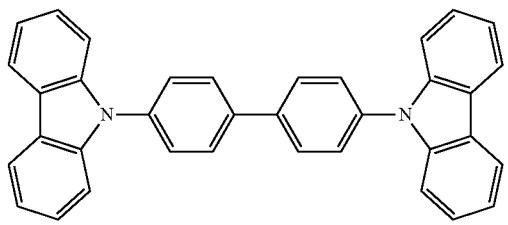

CBP

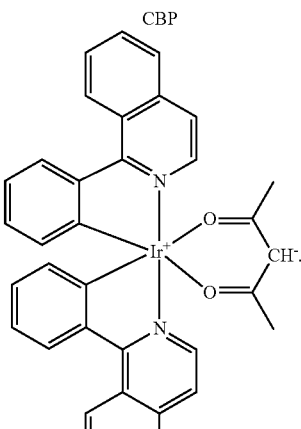

Ir(piq)2(acac)

Application Example 2

This application example differs from Application Example 1 in that the organic compound M1 in step (4) was replaced with an equal amount of organic compound M2, and other preparation steps were the same.

Application Example 3

This application example differs from Application Example 1 in that the organic compound M1 in step (4) was replaced with an equal amount of organic compound M3, and other preparation steps were the same.

Application Example 4

This application example differs from Application Example 1 in that the organic compound M1 in step (4) was replaced with an equal amount of organic compound M4, and other preparation steps were the same.

Comparative Example 1

This comparative example differs from Application Example 1 in that the organic compound M1 in step (4) was replaced with an equal amount of comparative compound CBP

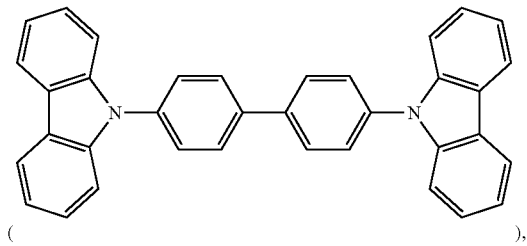 [SMILES: c1ccc2c(c1)c1ccccc1n2-c1ccc(-c2ccc(-n3c4ccccc4c4ccccc43)cc2)cc1]

( ), and other preparation steps were the same.

Comparative Example 2

This comparative example differs from Application Example 1 in that the organic compound M1 in step (4) was replaced with an equal amount of comparative compound TCTA

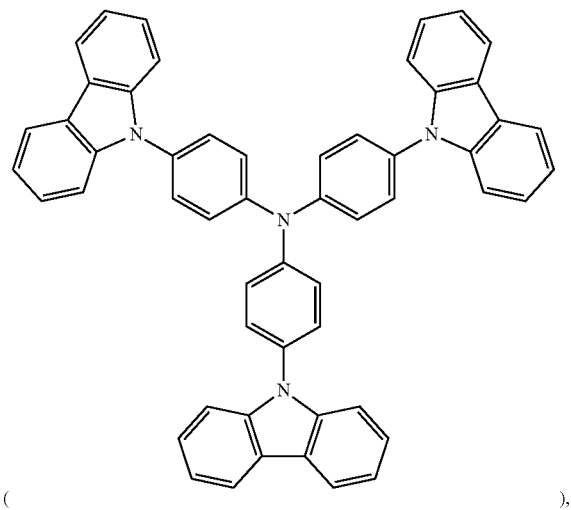 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

( ), and other preparation steps were the same.

Performance Test:

(1) Simulated Calculations of Compounds

An energy level difference between a singlet state and a triplet state of an organic compound may be completed by Guassian 09 software (produced by Guassian Inc.). A specific simulation method of the energy level difference $\Delta E_{ST}$ may be referred to Document J. Chem. Comput., 2013, DOI: 10.1021/ct400415r. The optimization and excitation of a molecular structure may both be completed by a TD-DFT method "B3LYP" and a basic group "6-31g (d)". The organic compounds M1, M2, M3, and M4 provided by the present disclosure were simulated according to the above-mentioned methods. Results are listed in Table 1.

The glass transition temperature $T_g$ (° C.) of the organic compound was measured by a thermogravimetric (TG) analysis, where a test instrument was Netzsch TG 209, and the organic compound was heated under nitrogen protection at a speed of 10° C.·min$^{-1}$. Test results are listed in Table 1.

TABLE 1

| Compound | HOMO (eV) | LUMO (eV) | $E_g$ (eV) | $T_1$ (eV) | $T_g$ (° C.) |
| --- | --- | --- | --- | --- | --- |
| M1 | −5.69 | −2.02 | 3.67 | 2.93 | 113 |
| M2 | −5.78 | −2.00 | 3.78 | 3.01 | 117 |
| M3 | −5.74 | −1.96 | 3.78 | 2.96 | 126 |
| M4 | −5.64 | −2.10 | 3.54 | 2.89 | 112 |

It can be seen from data in Table 1 that through a special design of the molecular structure, the organic compound of the present disclosure has appropriate HOMO energy level and LUMO energy level and a relatively high triplet energy levels $T_1$ which reaches 2.89 to 3.01 eV, and can inhabit the transfer of triplet energy from a guest back to a host, so as to confine triplet excitons in a light emitting layer and reduce a driving voltage of the device. Meanwhile, the organic compound has a relatively high glass transition temperature $T_g$ which reaches 112 to 126° C., which proves that the organic compound has good thermal stability and film formability.

(2) Performance Evaluation of OLED Devices

A Keithley 2365A digital nanovoltmeter was used for testing currents of the OLED devices at different voltages, and then the currents were divided by a light emitting area to obtain current densities of the OLED devices at different voltages. A Konicaminolta CS-2000 spectroradiometer was used for testing the brightness and radiant energy flux densities of the OLED devices at different voltages. According to the current densities and the brightness of the OLED devices at different voltages, a working voltage, current efficiency (cd/A), and external quantum efficiency (EQE, %) at the same current density (10 mA/cm$^2$) were obtained, where $V_{on}$ denotes a turn-on voltage under the brightness of 1 Cd/m$^2$. Specific data is listed in Table 2.

TABLE 2

| Device | Host Material of the Light Emitting Layer | $V_{turn-on}$ (V) | CE (Cd/A) | EQE (%) |
| --- | --- | --- | --- | --- |
| Application Example 1 | M1 | 3.6 | 37.8 | 23.1 |
| Application Example 2 | M2 | 3.5 | 41.3 | 25.2 |
| Application Example 3 | M3 | 3.7 | 39.2 | 24.3 |
| Application Example 4 | M4 | 3.6 | 35.9 | 23.5 |
| Comparative Example 1 | CBP | 4.2 | 31.3 | 19.6 |
| Comparative Example 2 | TATC | 4.5 | 29.8 | 17.9 |

It can be seen from data in Table 2 that compared with a host material CBP or TATC of the light emitting layer in the related art, the organic compounds provided by the present disclosure, as host materials of blue light emitting layers, enable the prepared OLED devices to have lower turn-on voltages (which decrease to 3.5 V to 3.7 V), higher current efficiency (which reaches 35.9 Cd/A to 41.3 Cd/A), and higher external quantum efficiency (which reaches 23.1% to 25.2%).

The applicant has stated that although the organic compound, the electroluminescent material and the use thereof in the present disclosure are described through the embodiments described above, the present disclosure is not limited to the processes and steps described above, which means that the implementation of the present disclosure does not necessarily depend on the processes and steps described above. It should be apparent to those skilled in the art that any improvements made to the present disclosure, equivalent replacements of raw materials selected in the present disclosure and addition of adjuvant ingredients thereof, and selections of specific methods, etc., all fall within the protection scope and the disclosed scope of the present disclosure.

What is claimed is:

1. An organic compound having a structure represented by Formula I:

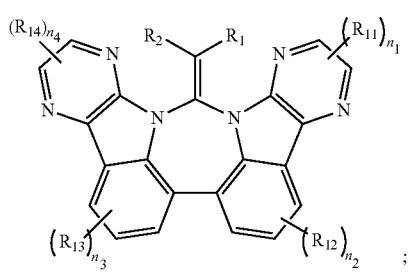

Formula I wherein $R_1$ and $R_2$ are each independently selected from any one of substituted or unsubstituted C6 to C30 aryl and substituted or unsubstituted C2 to C30 heteroaryl;
wherein $R_{11}$, $R_{12}$, $R_{13}$, and $R_{14}$ are each independently selected from any one of halogen, cyano, substituted or unsubstituted C1 to C20 straight or branched chain alkyl, C1 to C20 alkoxy, C1 to C20 alkylthio, substituted or unsubstituted C3 to C20 cycloalkyl, substituted or unsubstituted C6 to C30 aryl, and substituted or unsubstituted C2 to C30 heteroaryl;
wherein $n_1$ and $n_4$ are each independently selected from an integer between 0 and 2; and
wherein $n_2$ and $n_3$ are each independently selected from an integer between 0 and 3.

2. The organic compound according to claim 1, wherein substituents in substituted aryl, substituted heteroaryl, substituted straight or branched chain alkyl, and substituted cycloalkyl are each independently selected from at least one of halogen, cyano, halogenated or unsubstituted C1 to C10 straight or branched chain alkyl, C6 to C18 aryl, C2 to C18 heteroaryl, C6 to C18 arylamino, C1 to C10 alkoxy, and C1 to C10 alkylthio.

3. The organic compound according to claim 1, wherein $R_1$ and $R_2$ are each independently selected from any one of the following groups or any one of the following groups substituted with a substituent:

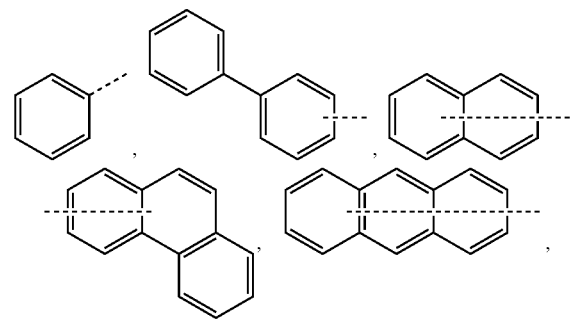

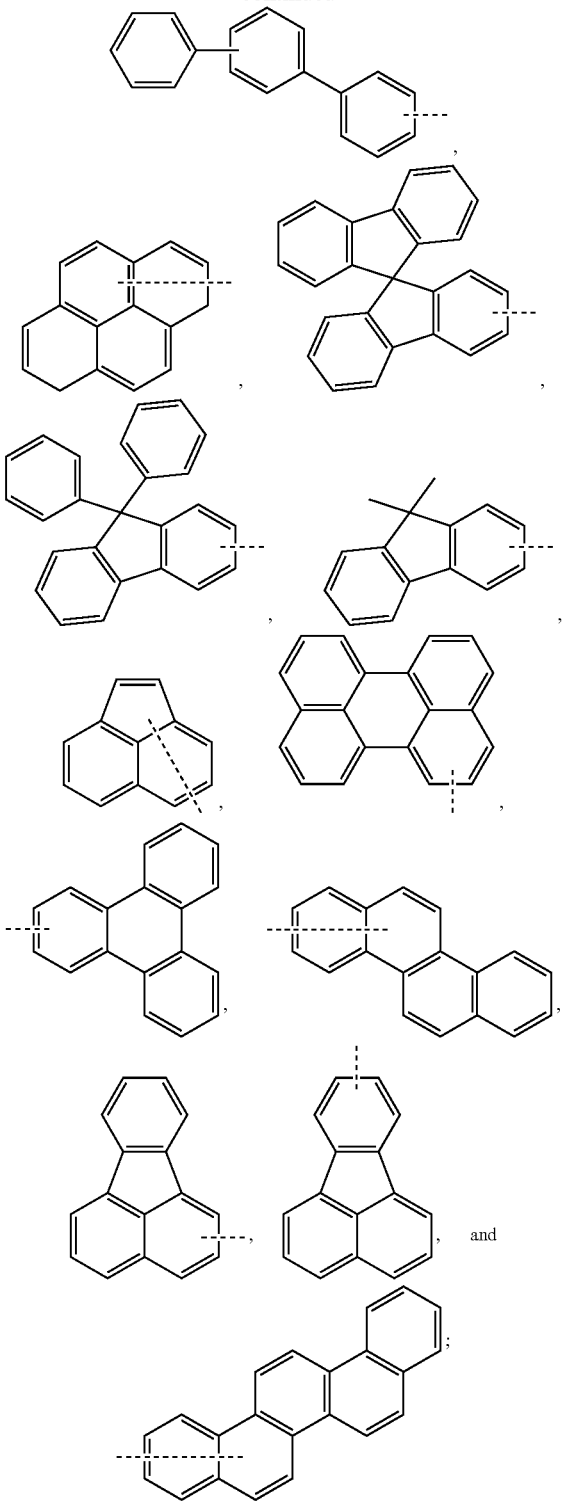

wherein the dashed line represents a linkage site of the group; and wherein the substituent is selected from at least one of halogen, cyano, halogenated or unsubstituted C1 to C10 straight or branched chain alkyl, C6 to C18 aryl, C2 to C18 heteroaryl, C1 to C10 alkoxy, and C1 to C10 alkylthio.

4. The organic compound according to claim 1, wherein R₁ and R₂ are each independently selected from any one of the following groups:

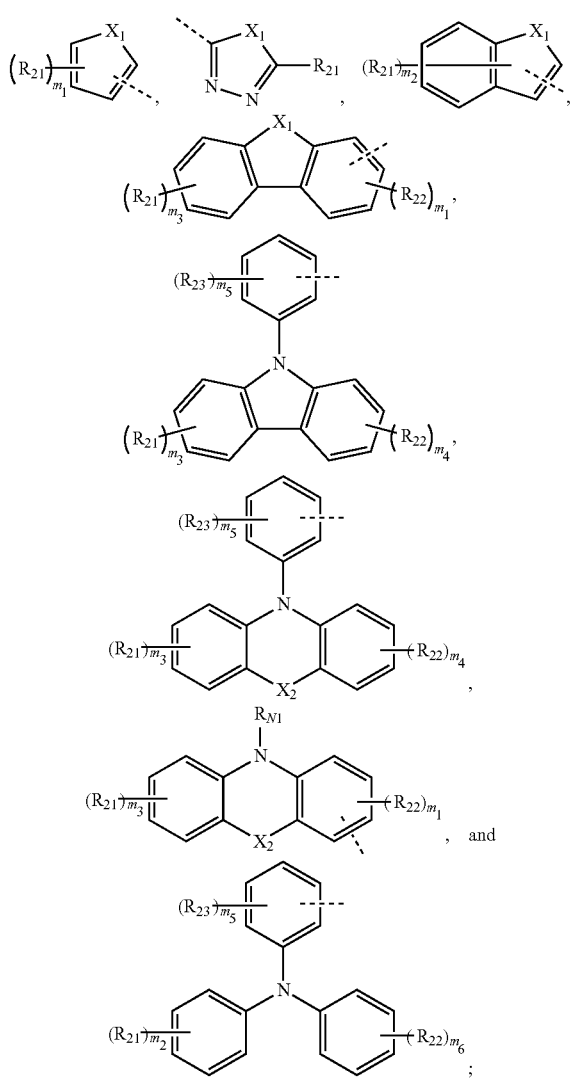

wherein the dashed line represents a linkage site of the group;
wherein $X_1$ is selected from O, S, or N—$R_{N2}$;
wherein $X_2$ is selected from O, S, N—$R_{N3}$, or $CR_{C1}R_{C2}$;
wherein $R_{N1}$, $R_{N2}$, $R_{N3}$, $R_{C1}$, and $R_{C2}$ are each independently selected from hydrogen, unsubstituted or $R_{x1}$-substituted C1 to C10 straight or branched chain alkyl, unsubstituted or $R_{x1}$-substituted C6 to C18 aryl, or unsubstituted or $R_{x1}$-substituted C2 to C18 heteroaryl;
wherein $R_{21}$, $R_{22}$, $R_{23}$, and $R_{x1}$ are each independently selected from any one of halogen, cyano, halogenated or unsubstituted C1 to C10 straight or branched chain alkyl, C6 to C18 aryl, C2 to C18 heteroaryl, C6 to C18 arylamino, C1 to C10 alkoxy, and C1 to C10 alkylthio;
wherein $m_1$ is selected from an integer between 0 and 3;
wherein $m_2$ and $m_6$ are each independently selected from an integer between 0 and 5; and
wherein $m_3$, $m_4$, and $m_5$ are each independently selected from an integer between 0 and 4.

5. The organic compound according to claim 4, wherein R₁ and R₂ are each independently selected from any one of the following groups or any one of the following groups substituted with a substituent:

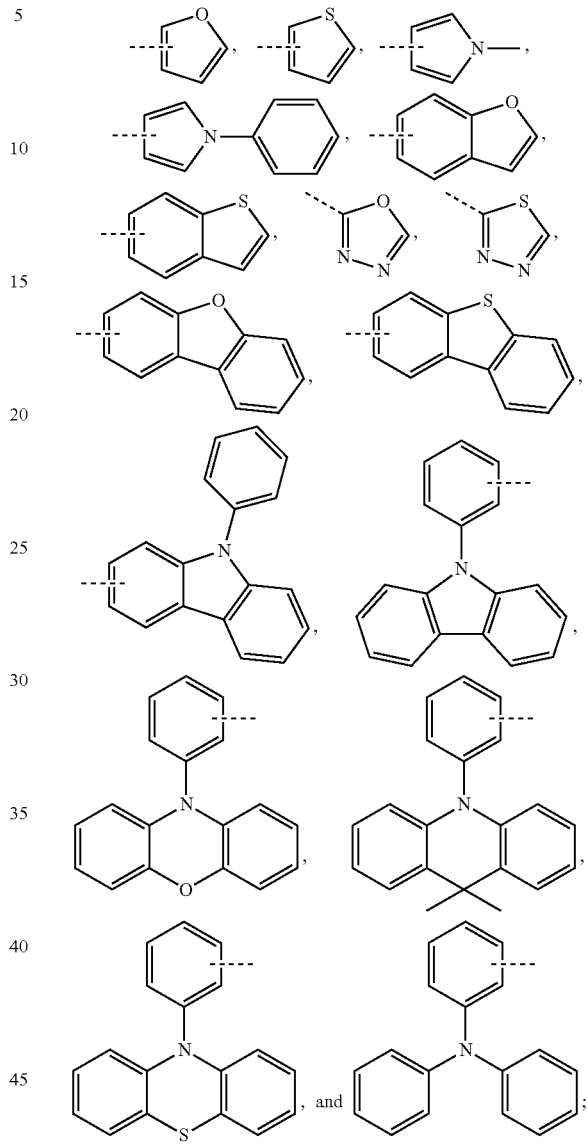

wherein the dashed line represents a linkage site of the group; and wherein the substituent is selected from at least one of halogen, cyano, halogenated or unsubstituted C1 to C10 straight or branched chain alkyl, C6 to C18 aryl, C2 to C18 heteroaryl, C1 to C10 alkoxy, and C1 to C10 alkylthio.

6. The organic compound according to claim 1, wherein R₁ and R₂ are each independently selected from any one of the following groups:

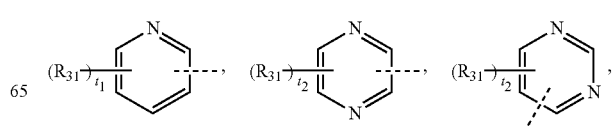

-continued

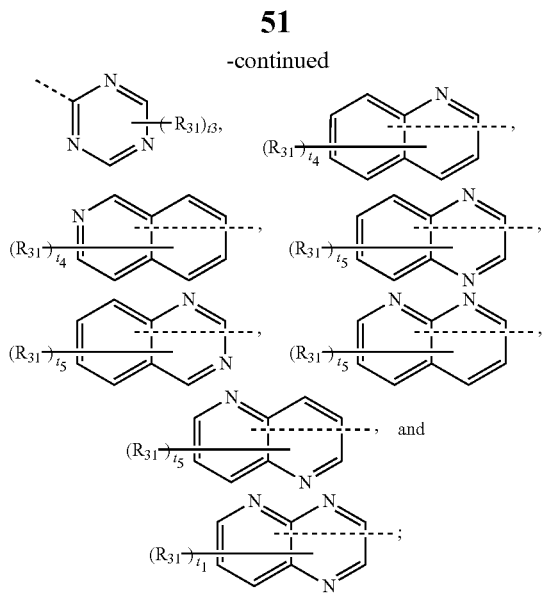

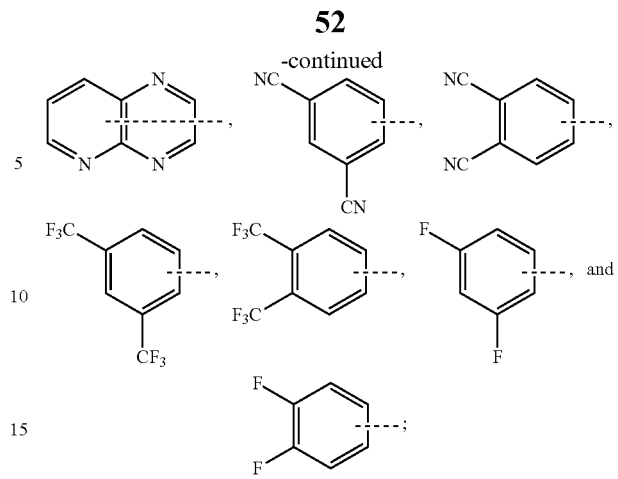

wherein the dashed line represents a linkage site of the group;
wherein $R_{31}$ is each independently selected from any one of halogen, cyano, halogenated or unsubstituted C1 to C10 straight or branched chain alkyl, C6 to C18 aryl, C2 to C18 heteroaryl, C1 to C10 alkoxy, and C1 to C10 alkylthio;
wherein $t_1$ is selected from an integer between 0 and 4;
wherein $t_2$ is selected from an integer between 0 and 3;
wherein $t_3$ is selected from an integer between 0 and 2;
wherein $t_4$ is selected from an integer between 0 and 6; and
wherein $t_5$ is selected from an integer between 0 and 5.

7. The organic compound according to claim 1, wherein $R_1$ and $R_2$ are each independently selected from any one of the following groups or any one of the following groups substituted with a substituent:

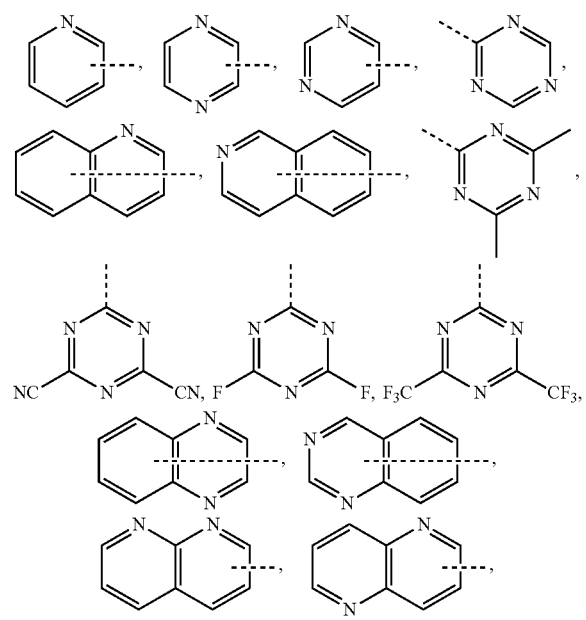

wherein the dashed line represents a linkage site of the group; and
wherein the substituent is selected from at least one of halogen, cyano, halogenated or unsubstituted C1 to C10 straight or branched chain alkyl, C6 to C18 aryl, C2 to C18 heteroaryl, C1 to C10 alkoxy, and C1 to C10 alkylthio.

8. The organic compound according to claim 1, wherein $R_1$ and $R_2$ are the same substituent.

9. The organic compound according to claim 1, wherein at least one of $R_1$ and $R_2$ is an electron withdrawing group.

10. The organic compound according to claim 1, wherein $R_{11}$, $R_{12}$, $R_{13}$, and $R_{14}$ are each independently selected from halogen, cyano, substituted or unsubstituted C1 to C5 straight or branched chain alkyl, substituted or unsubstituted C6 to C12 aryl, and substituted or unsubstituted C2 to C12 heteroaryl; and the substituent is selected from at least one of halogen, cyano, halogenated or unsubstituted C1 to C5 straight or branched chain alkyl.

11. The organic compound according to claim 10, wherein $R_{11}$, $R_{12}$, $R_{13}$, and $R_{14}$ are each independently selected from any one of halogen, cyano, C1 to C3 straight or branched chain alkyl, unsubstituted or R'-substituted phenyl, unsubstituted or R'-substituted biphenyl, unsubstituted or R'-substituted naphthyl, unsubstituted or R'-substituted pyridyl, unsubstituted or R'-substituted pyrazinyl, unsubstituted or R'-substituted triazinyl, unsubstituted or R'-substituted quinolyl, unsubstituted or R'-substituted isoquinolyl, unsubstituted or R'-substituted benzoxazolyl, unsubstituted or R'-substituted pyrimidinyl; wherein R' is selected from halogen or cyano.

12. The organic compound according to claim 1, wherein the organic compound is selected from any one of the following compounds M1 to M80:

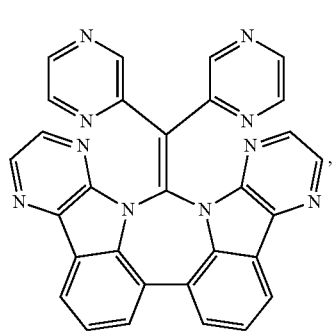

M1

M2
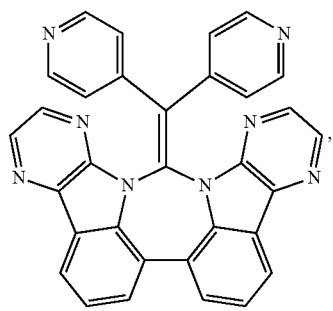
M3
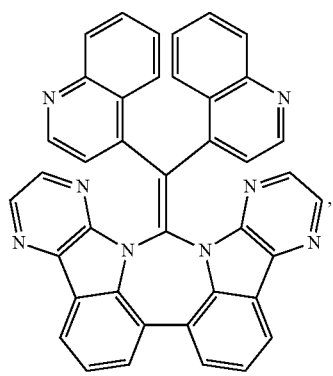
M4
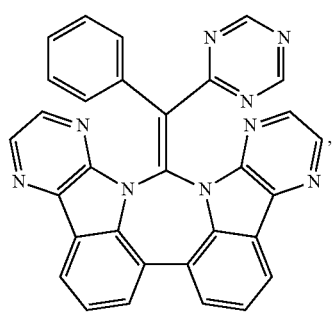
M5
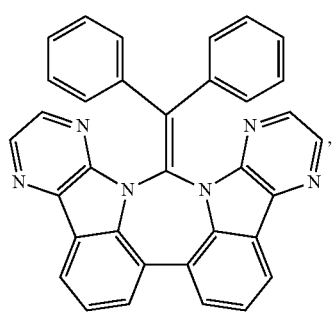
M6
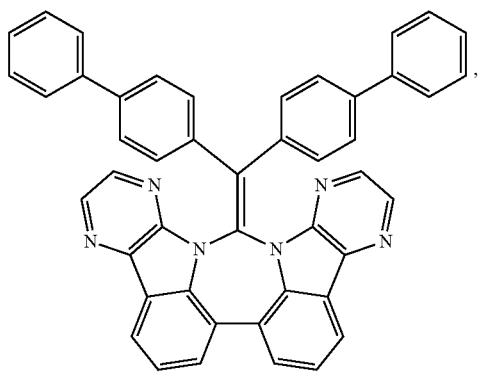
,
M7
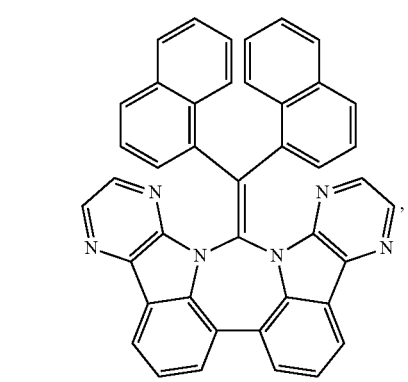
,
M8
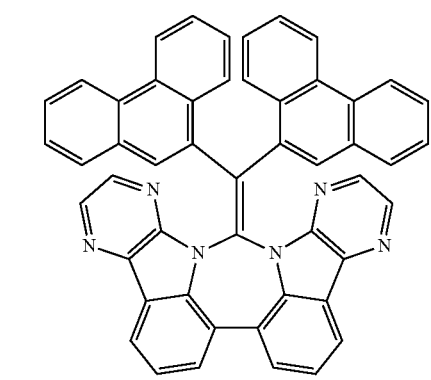
,
M9
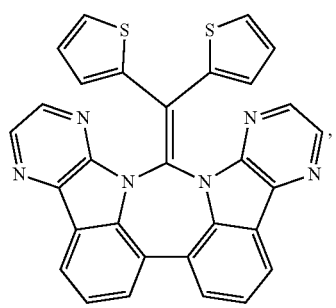
,

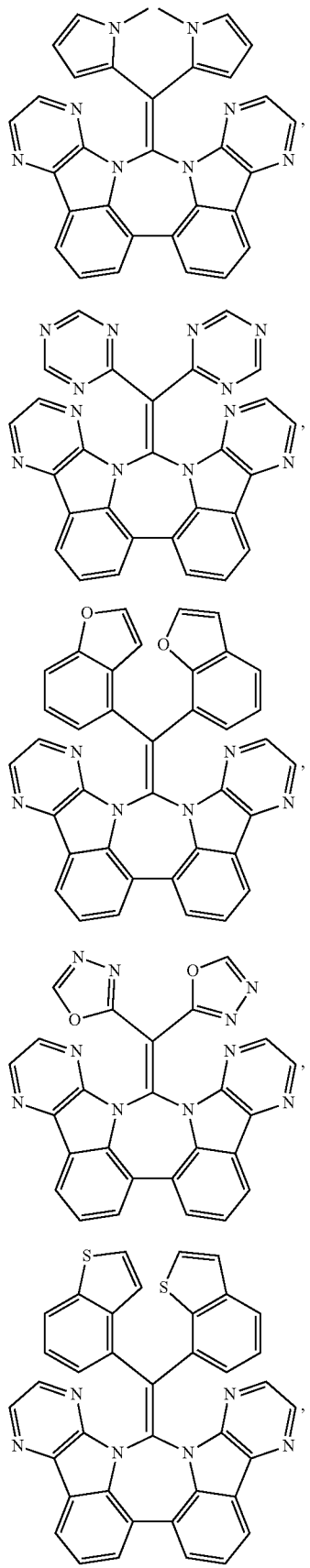
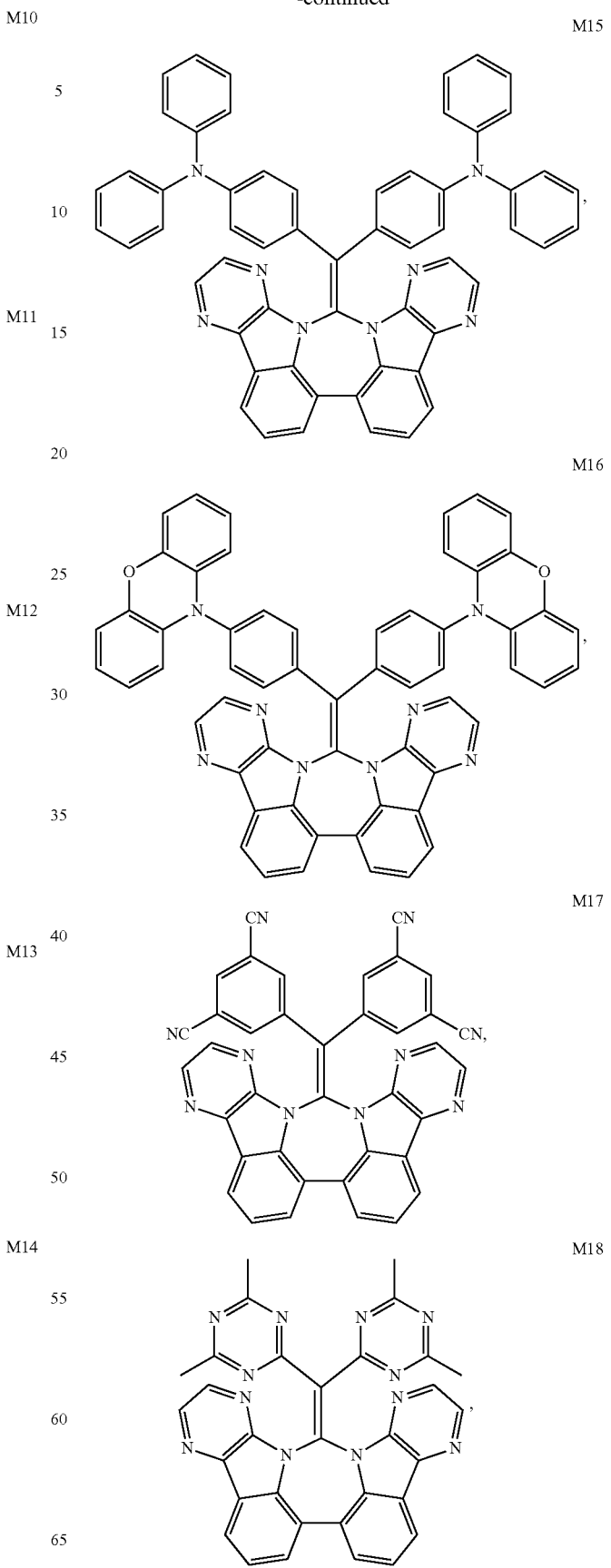

-continued
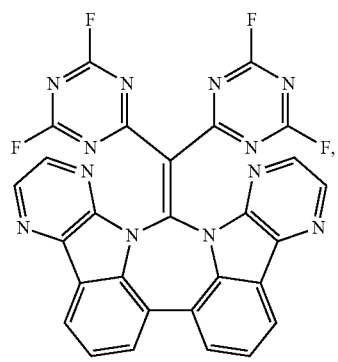
M19
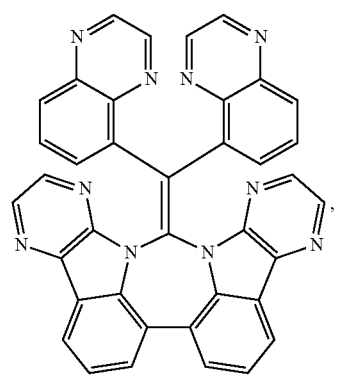
M20
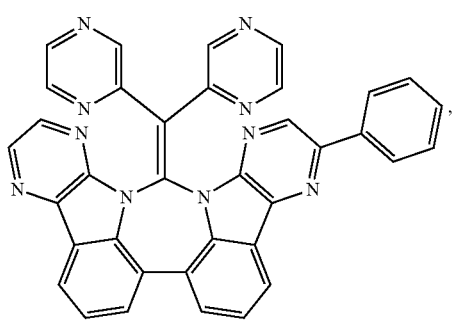
M21
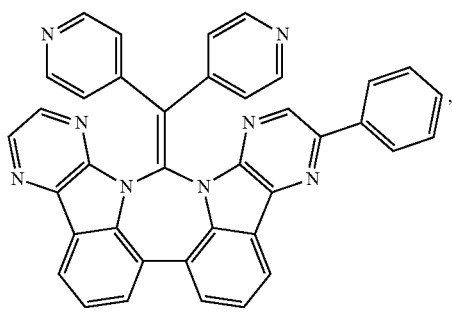
M22
-continued
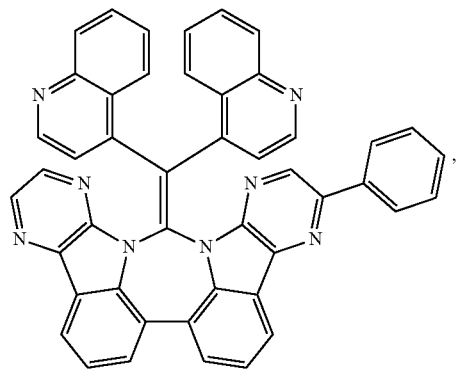
M23
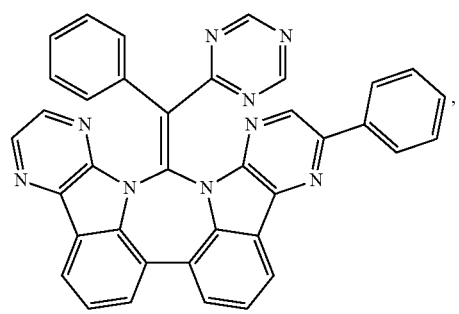
M24
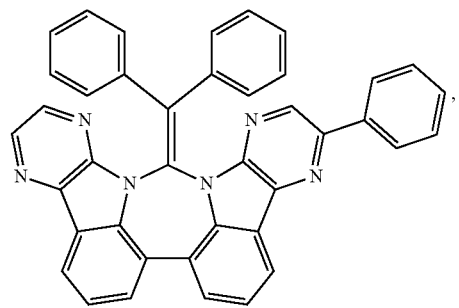
M25
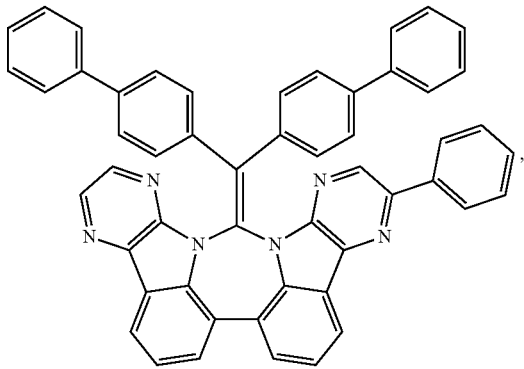
M26

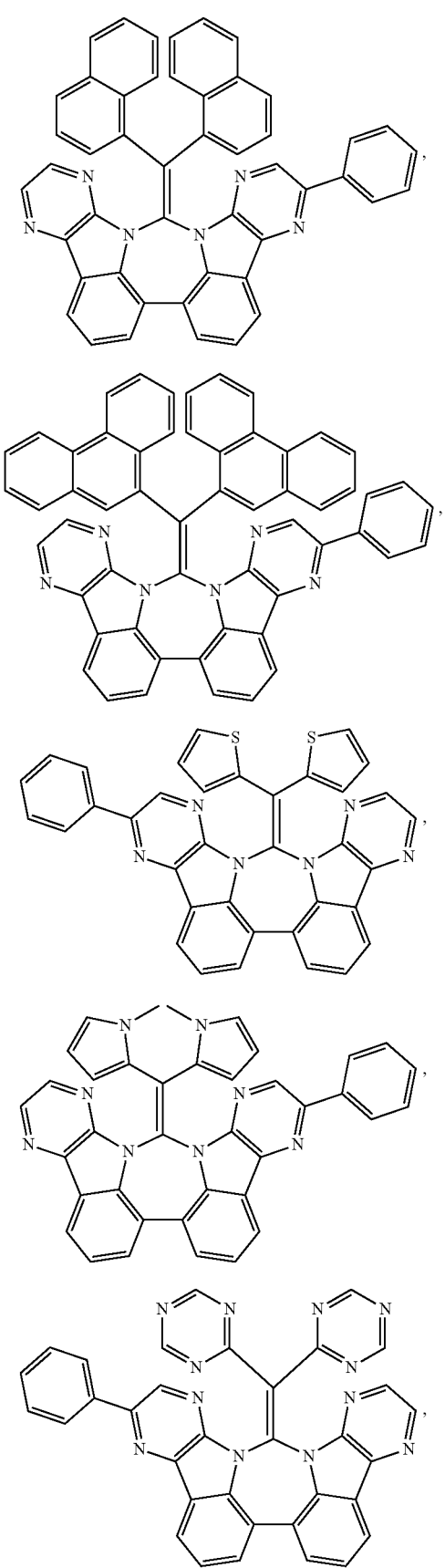
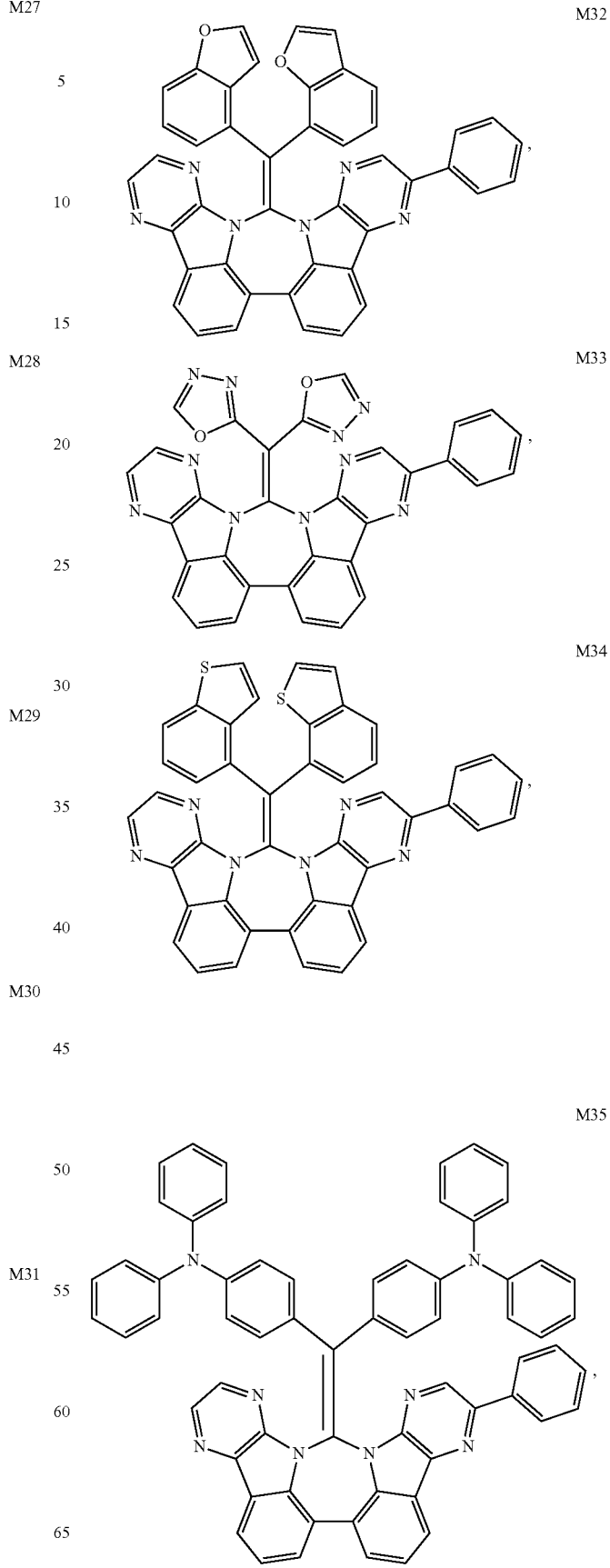

M36
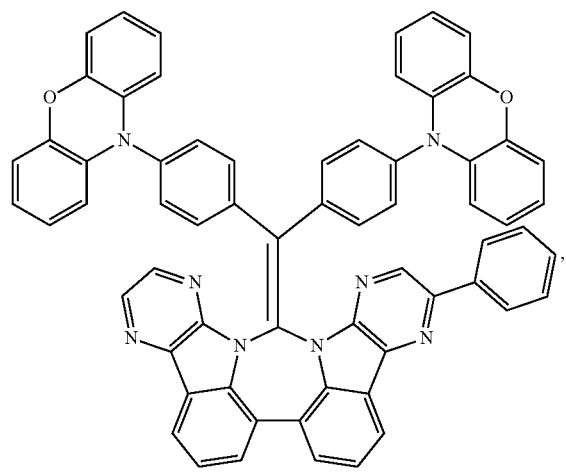
M37
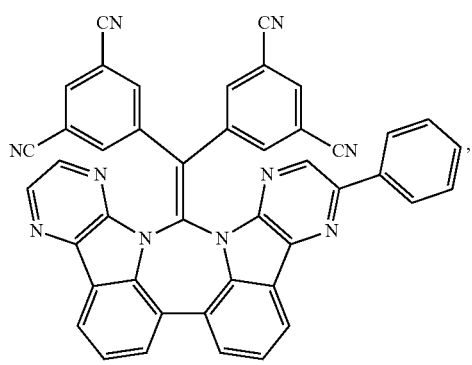
M38
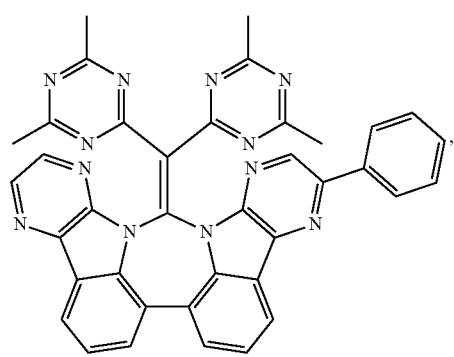
M39
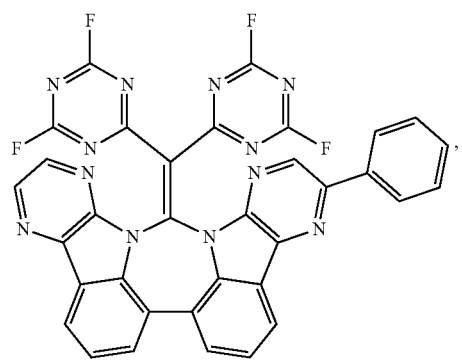
M40
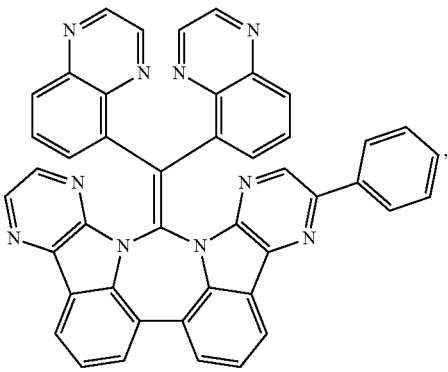
M41
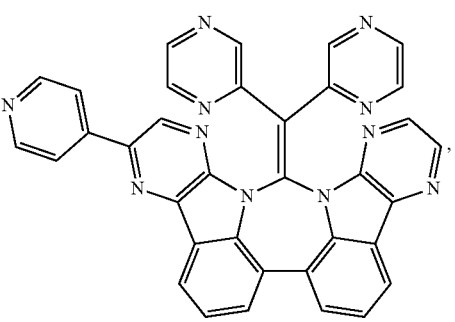
M42
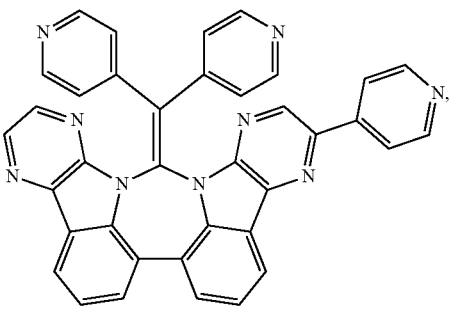
M43
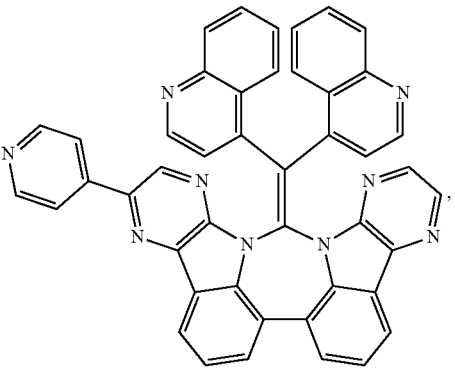

M44
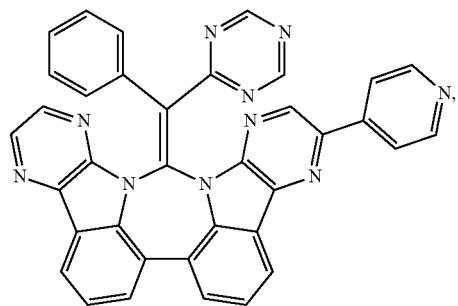
M45
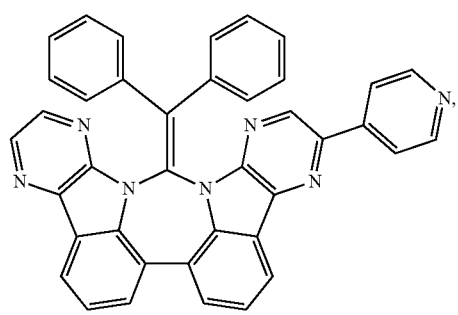
M46
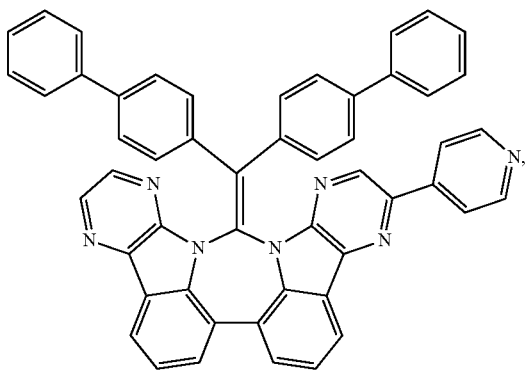
M47
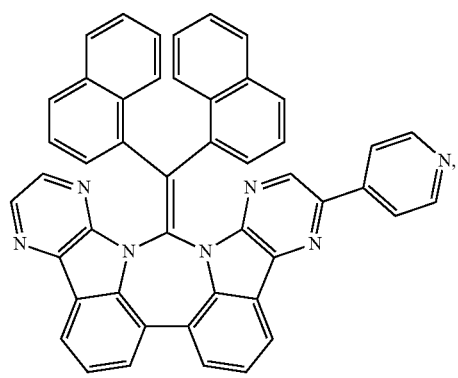
M48
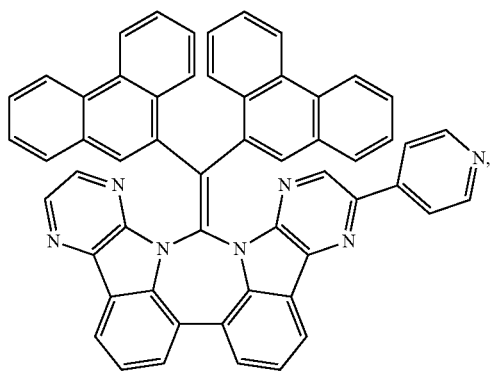
M49
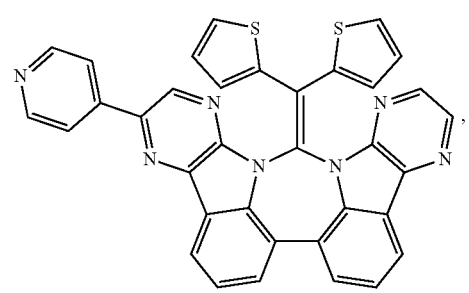
M50
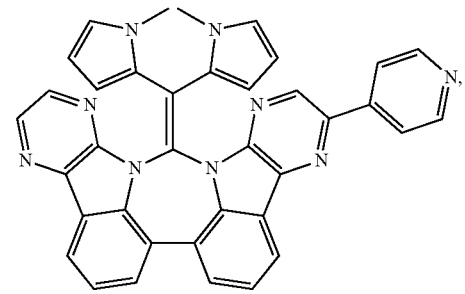
M51
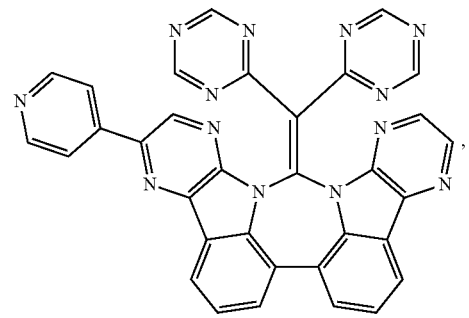
M52
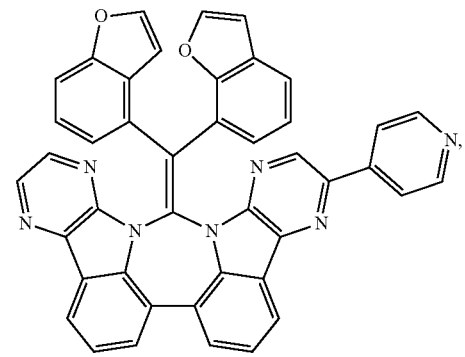

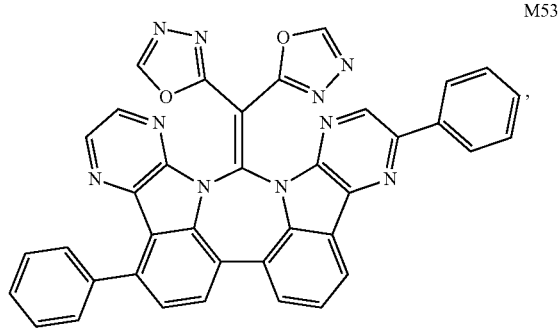
M53
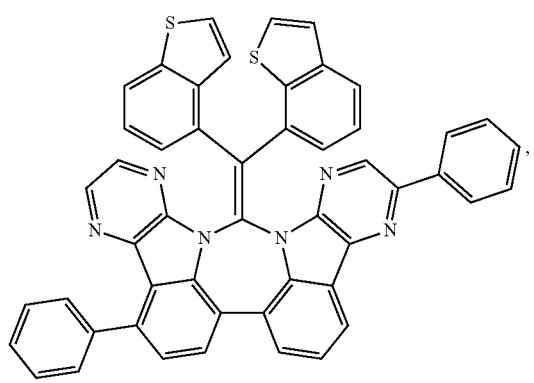
M54
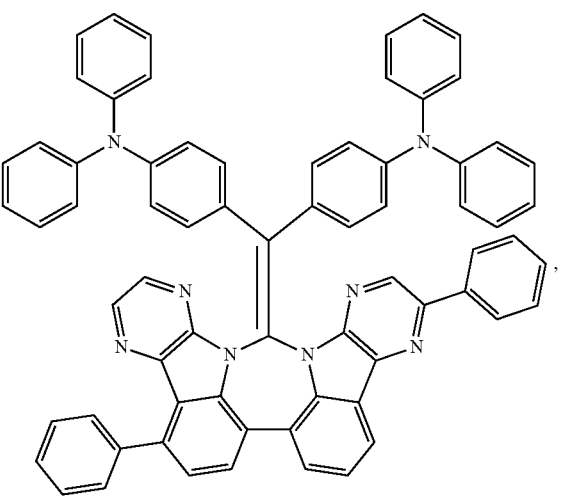
M55
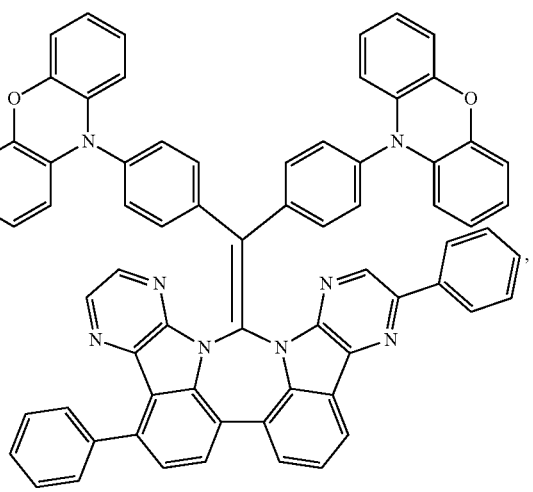
M56
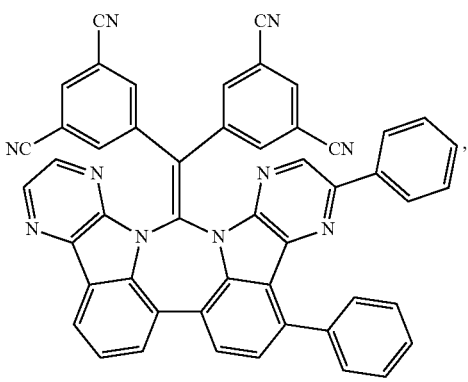
M57
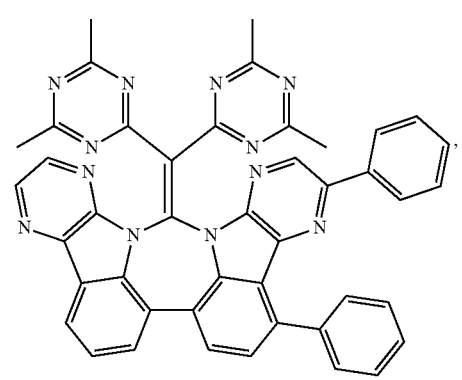
M58
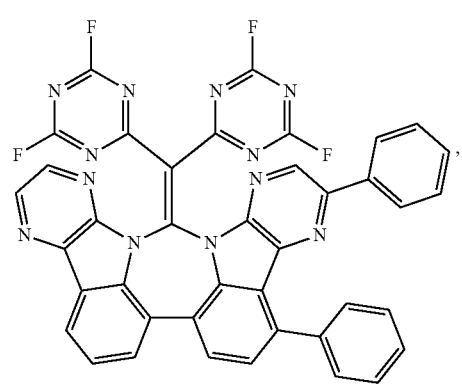
M59

M60
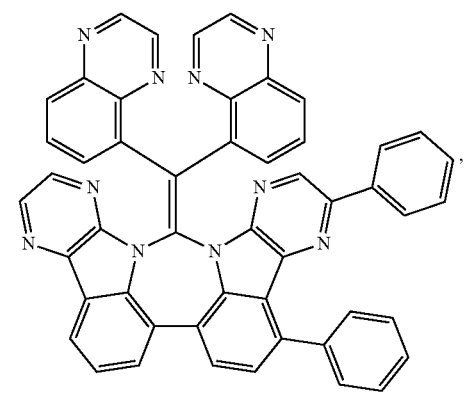
M61
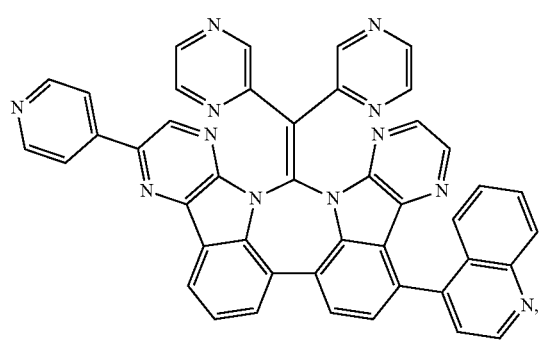
M62
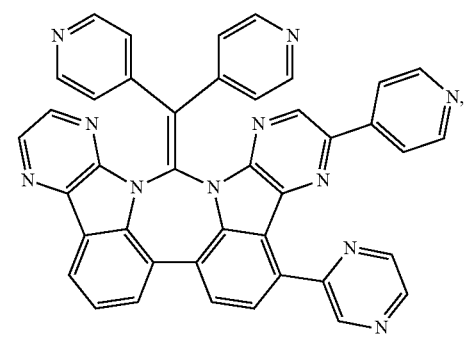
M63
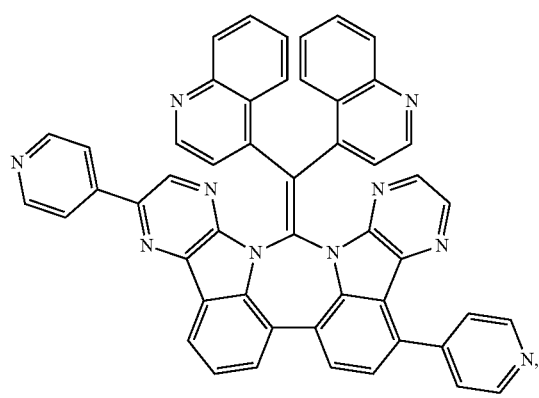
M64
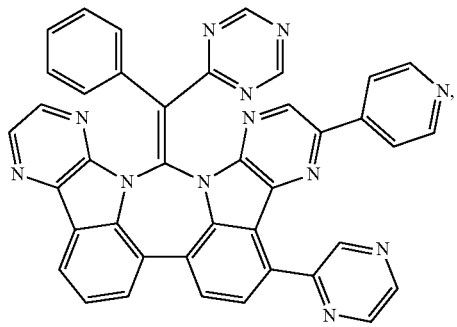
M65
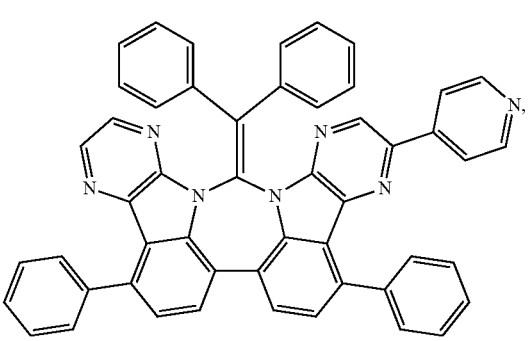
M66
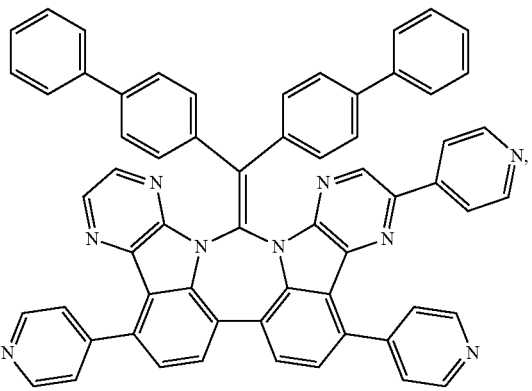
M67
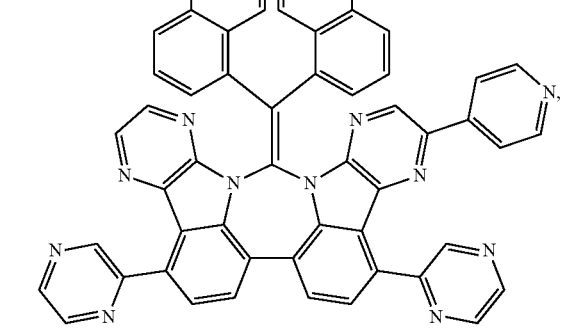

-continued
M68
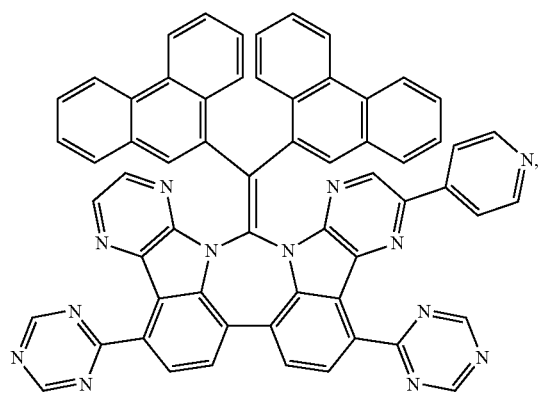
M69
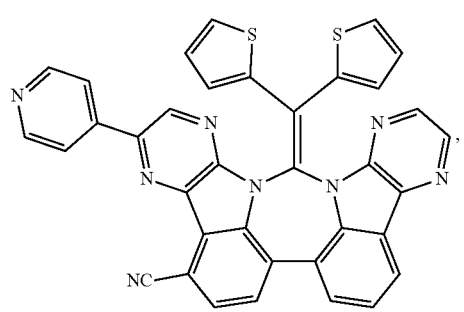
M70
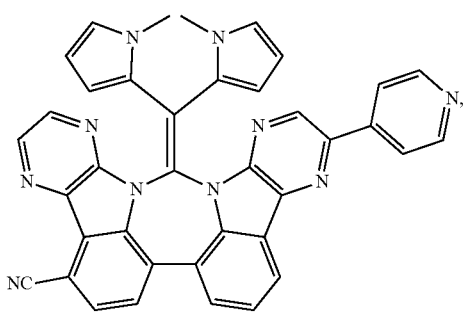
M71
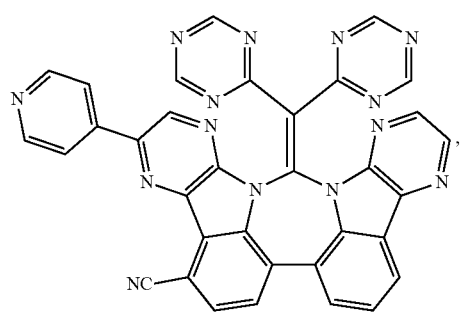
-continued
M72
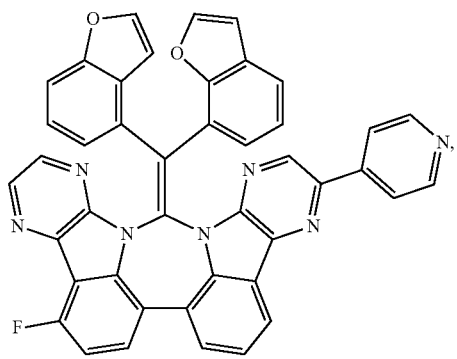
M73
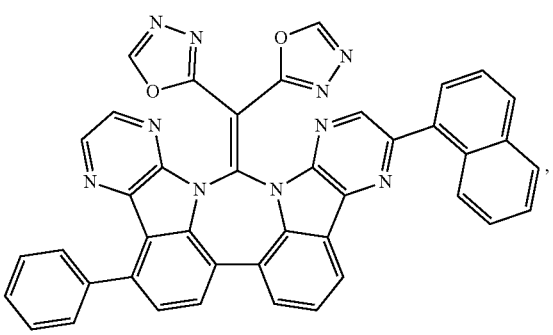
M74
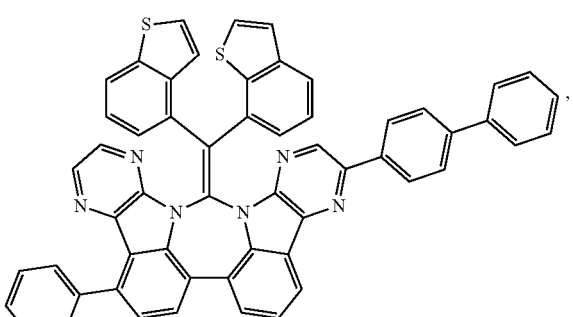
M75
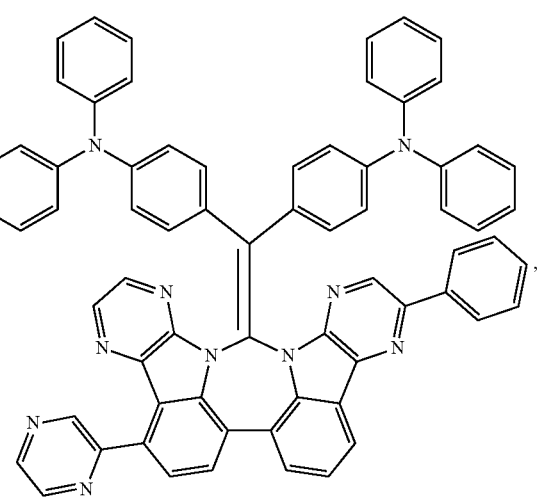

-continued

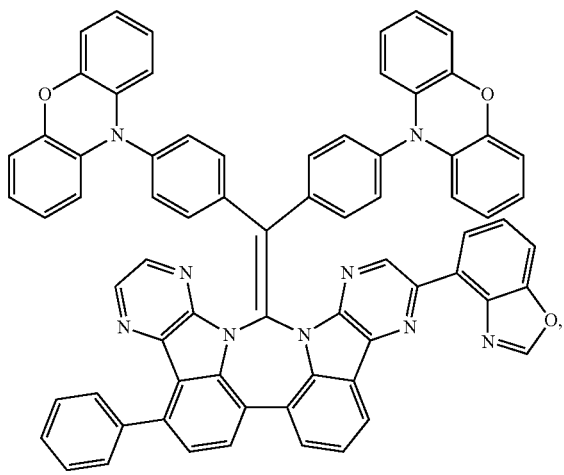

M76

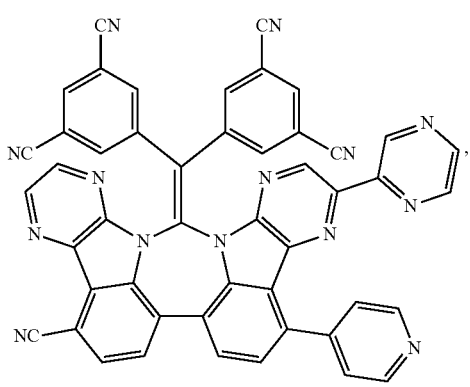

M77

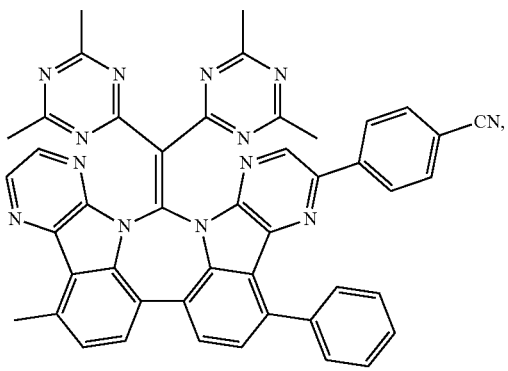

M78

-continued

M79

M80

13. An electroluminescent material, comprising the organic compound according to claim 1.

14. A display panel, comprising an organic light emitting diode (OLED) device, wherein the OLED device comprises an anode, a cathode and an organic thin film layer disposed between the anode and the cathode, the organic thin film layer comprises a light emitting layer whose material comprises the electroluminescent material according to claim 13.

15. The display panel according to claim 14, wherein the electroluminescent material is used as a phosphorescent host material of the light emitting layer.

* * * * *